(12) United States Patent
Morio et al.

(10) Patent No.: US 12,059,576 B2
(45) Date of Patent: Aug. 13, 2024

(54) LIGHT BASED DENTAL TREATMENT DEVICE

(71) Applicants: Kimberly Ann Morio, Solon, IA (US); Kim Alan Brogden, Coralville, IA (US); Robert H. Sternowski, Cedar Rapids, IA (US)

(72) Inventors: Kimberly Ann Morio, Solon, IA (US); Kim Alan Brogden, Coralville, IA (US); Robert H. Sternowski, Cedar Rapids, IA (US)

(73) Assignee: DENTOSITY, LLC, Solon, IA (US)

( * ) Notice: Subject to any disclaimer, the term of this patent is extended or adjusted under 35 U.S.C. 154(b) by 227 days.

(21) Appl. No.: 17/277,450

(22) PCT Filed: Oct. 25, 2019

(86) PCT No.: PCT/US2019/058186
§ 371 (c)(1),
(2) Date: Mar. 18, 2021

(87) PCT Pub. No.: WO2020/087023
PCT Pub. Date: Apr. 30, 2020

(65) Prior Publication Data
US 2022/0032081 A1    Feb. 3, 2022

Related U.S. Application Data

(60) Provisional application No. 62/751,440, filed on Oct. 26, 2018.

(51) Int. Cl.
*A61N 5/067* (2006.01)
*A61N 5/06* (2006.01)

(52) U.S. Cl.
CPC ...... *A61N 5/067* (2021.08); *A61N 2005/0606* (2013.01); *A61N 2005/0651* (2013.01); *A61N 2005/0658* (2013.01)

(58) Field of Classification Search
CPC ............ A61N 5/067; A61N 2005/0606; A61N 2005/0651; A61N 2005/0658; A61N 2005/0662; A61C 1/0046
See application file for complete search history.

(56) References Cited

U.S. PATENT DOCUMENTS 5,232,366 A    8/1993 Levy
5,503,559 A    4/1996 Vari
(Continued)

FOREIGN PATENT DOCUMENTS

| EP | 0253812 A1 | 1/1988 | |
|---|---|---|---|
| WO | WO-2017139256 A1 * | 8/2017 | ......... A46B 15/0012 |
| WO | 2018009864 | 1/2018 | |

OTHER PUBLICATIONS

European Search Report dated Jun. 10, 2022 from counterpart European Patent Application No. 19874953.3.
(Continued)

*Primary Examiner* — Carl H Layno
*Assistant Examiner* — Aya Ziad Bakkar
(74) *Attorney, Agent, or Firm* — Nyemaster Goode, P.C.

(57) ABSTRACT

A light-based dental treatment system includes a handle generator having a generator housing and at least one light element configured to generate therapeutic light. The handle generator includes an alignment collet having a light passage extending along a movable interior collet profile. At least one delivery shaft assembly is selectively coupled with the handle generator. The at least one delivery shaft assembly includes a delivery shaft having proximal and distal shaft profile and a proximal light port. A distal light port of the delivery shaft is configured to deliver therapeutic light from the delivery shaft to a treatment location. The interior collet profile of the alignment collet is configured to grasp the delivery shaft and align the proximal light port with the at least one light element.

26 Claims, 19 Drawing Sheets

(56) References Cited

U.S. PATENT DOCUMENTS

| | | |
|---|---|---|
| 2005/0196721 A1 | 9/2005 | Jackson |
| 2007/0027443 A1 | 2/2007 | Rose et al. |
| 2009/0191504 A1 | 7/2009 | Mannino |
| 2010/0160838 A1* | 6/2010 | Krespi .................. A61B 18/26 604/20 |
| 2010/0330523 A1 | 12/2010 | Kert |

OTHER PUBLICATIONS

International Search Report and Written Opinion of the International Authority, Patent Cooperation Treaty Application No. PCT/US2019/058186, Oct. 25, 2019.
Industrial Fiber Optics, Inc., Plastic Optical Fiber Connector IF-C-S2/S3/S4, dated May 22, 2004, www.i-fiberoptics.com.

* cited by examiner

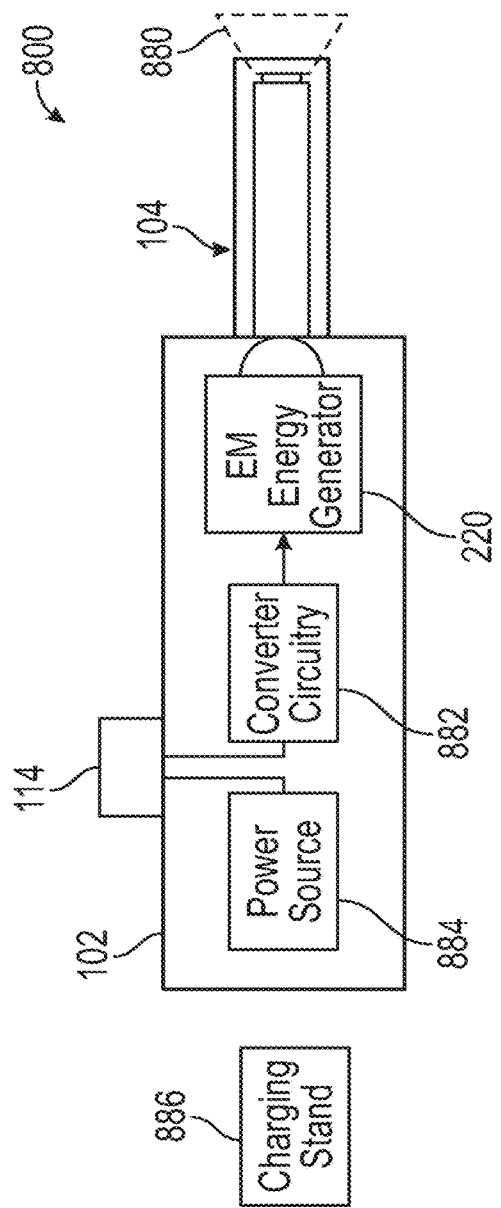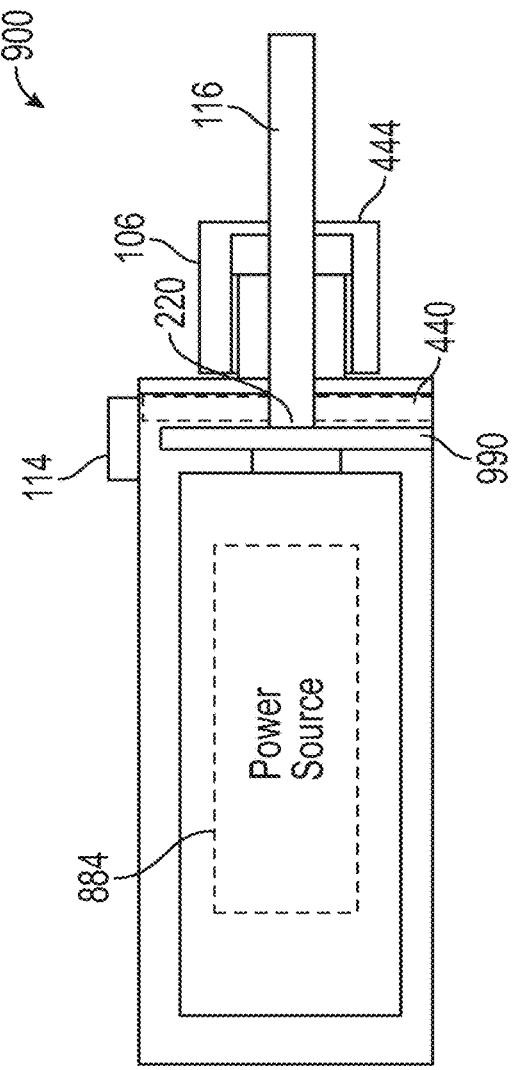

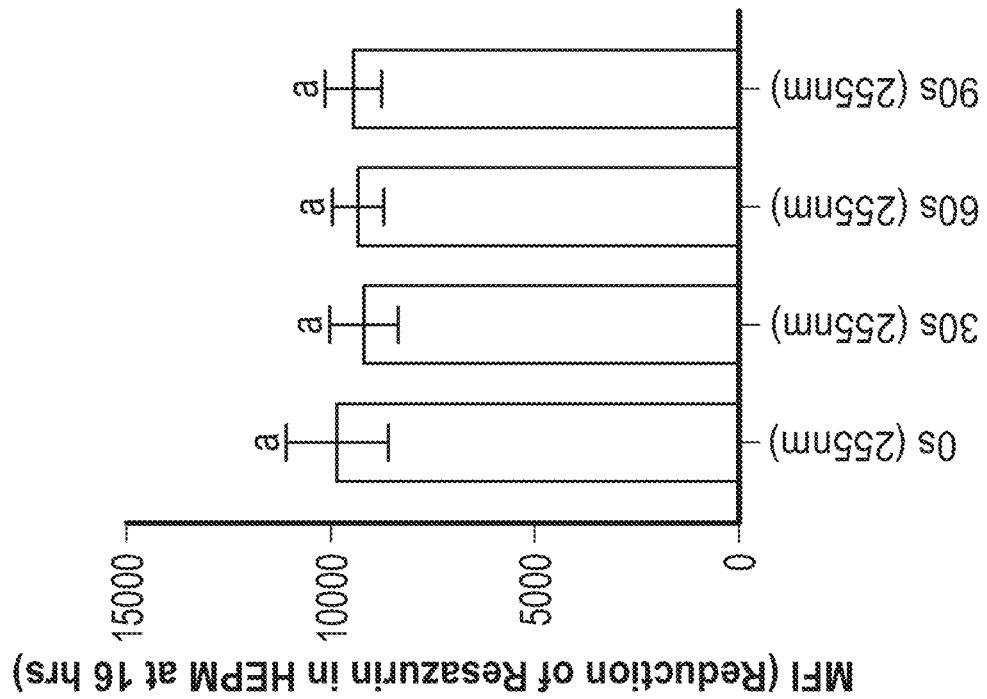
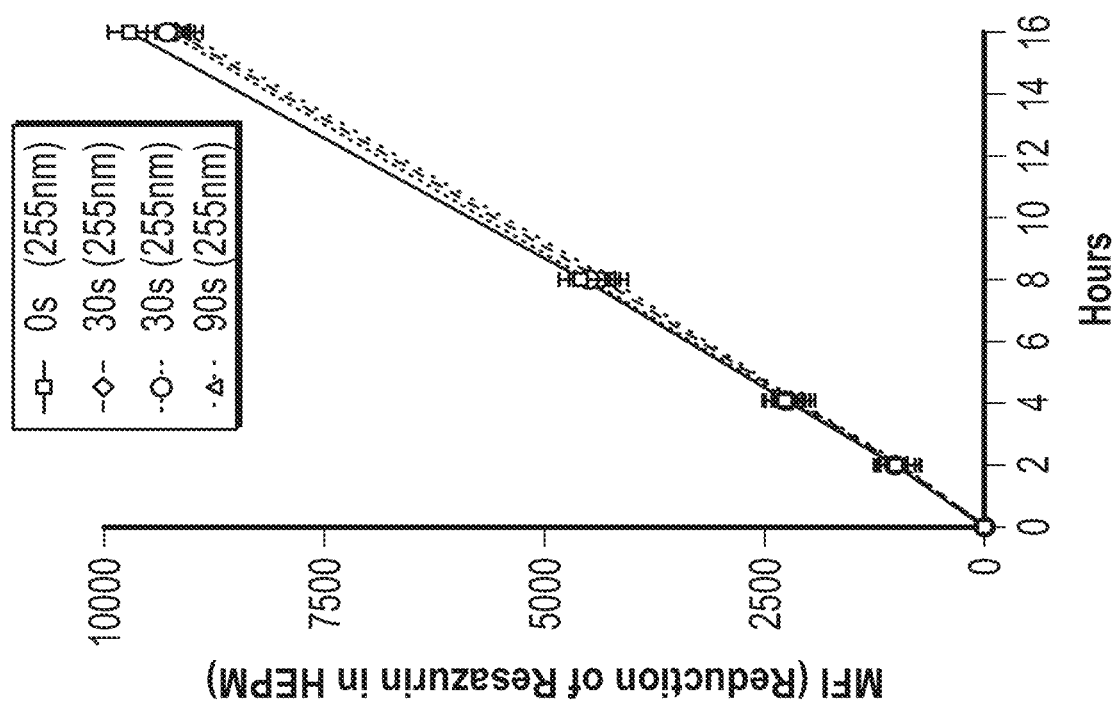
FIG. 13A

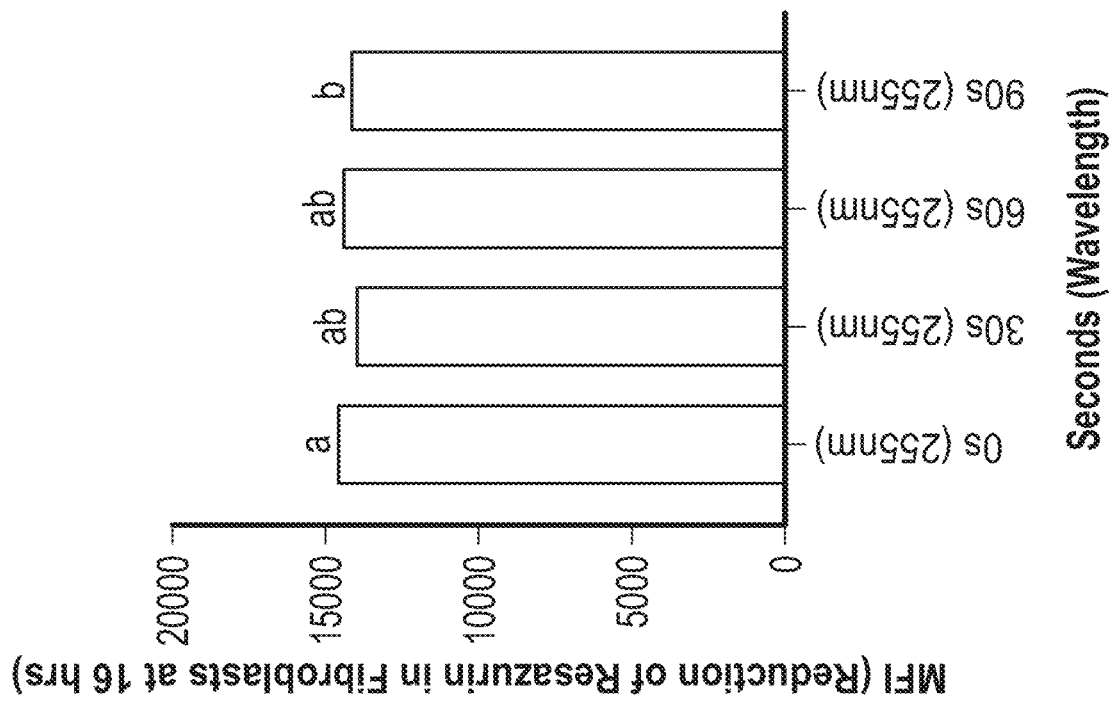
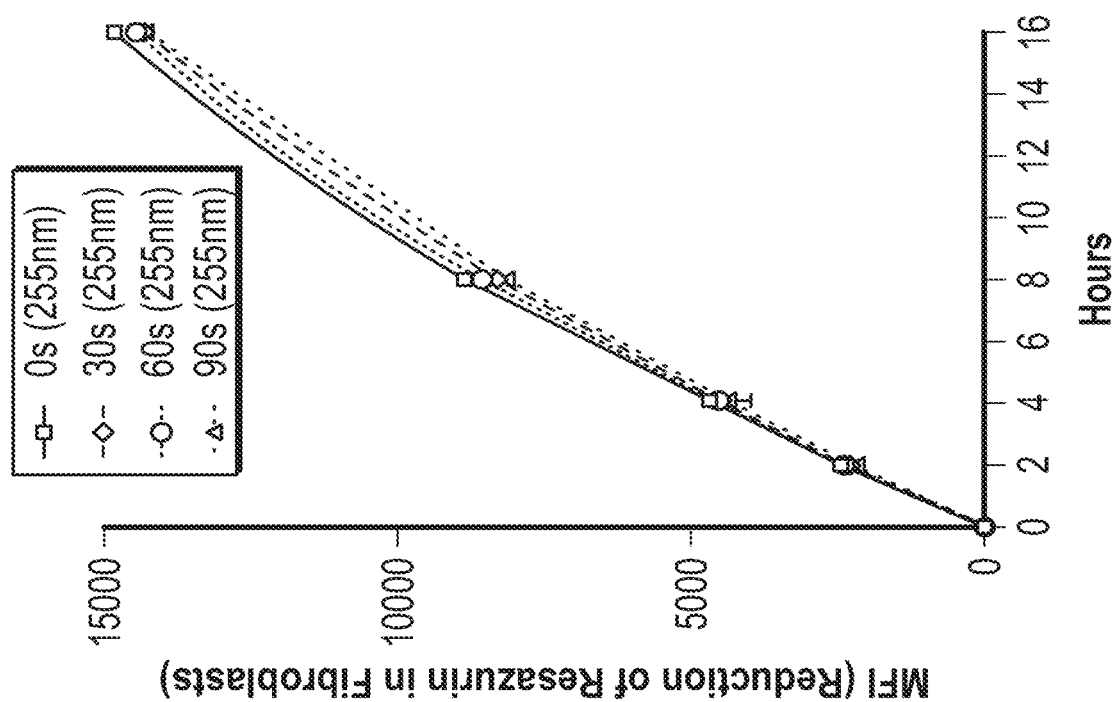
FIG. 13B

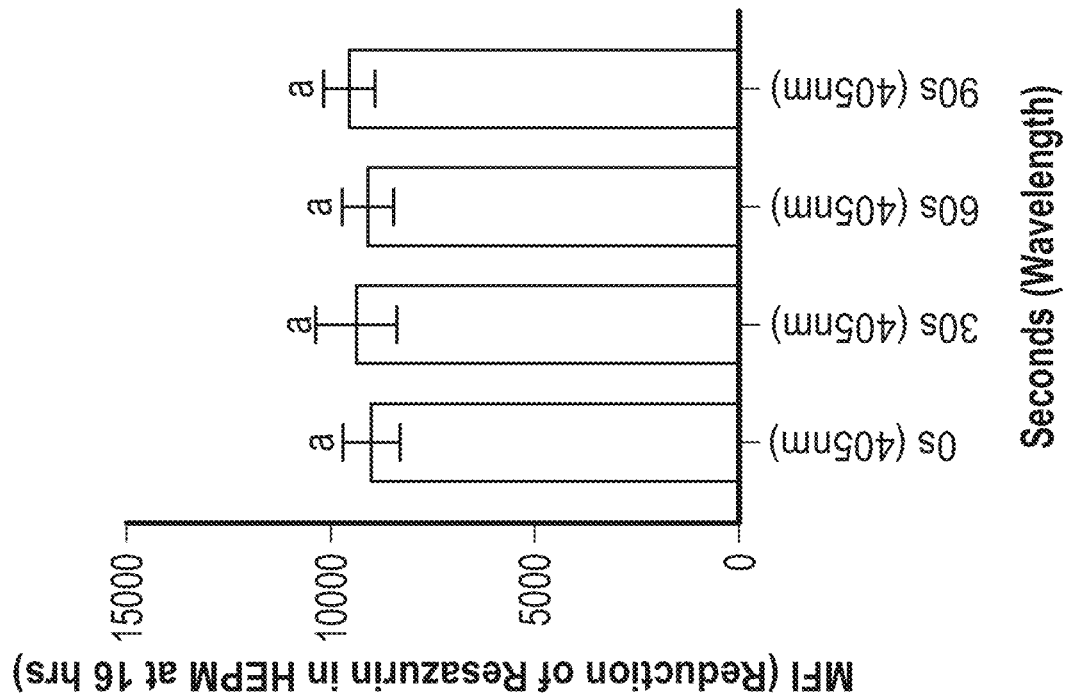
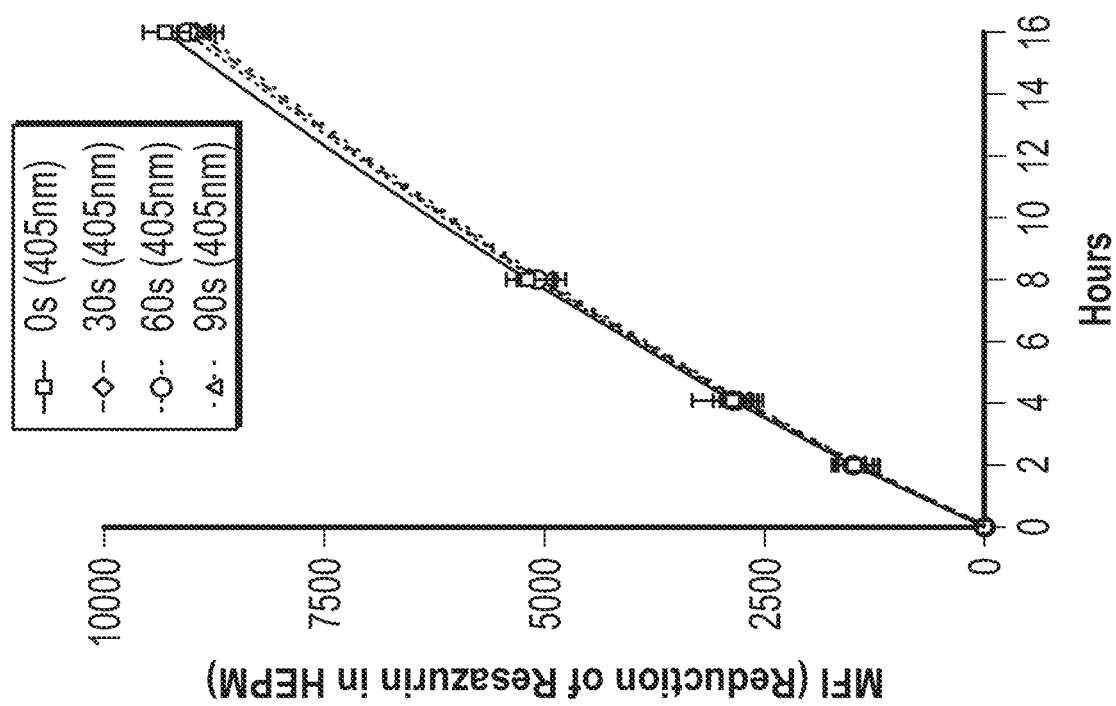
FIG. 13C

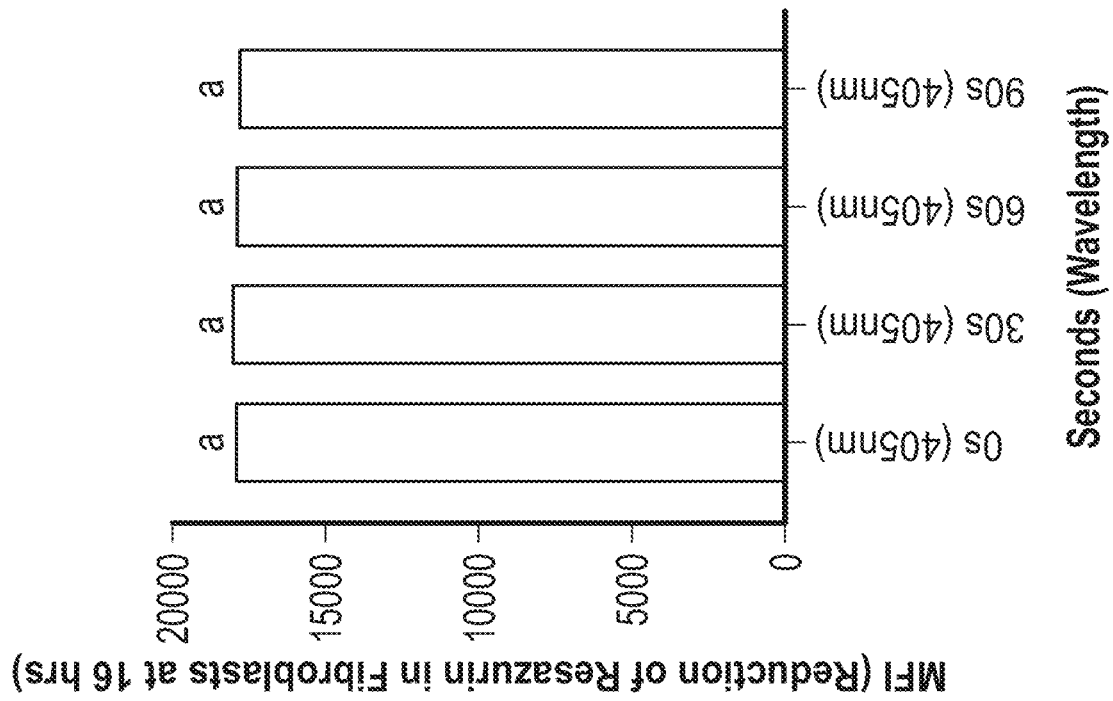
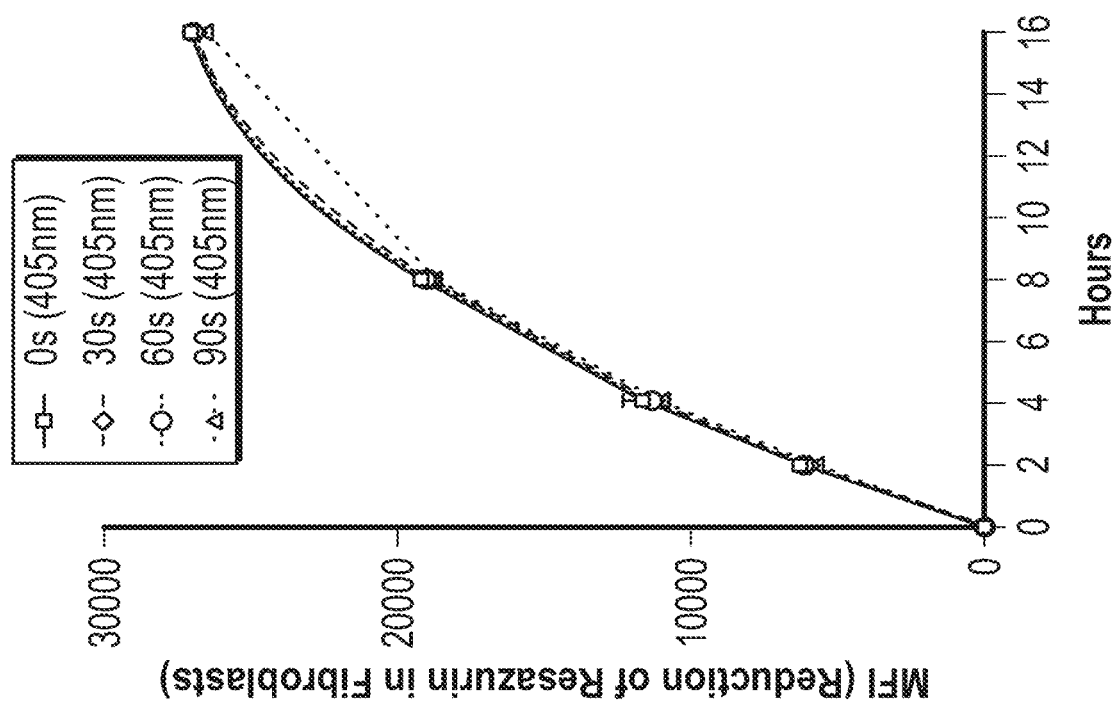
FIG. 13D

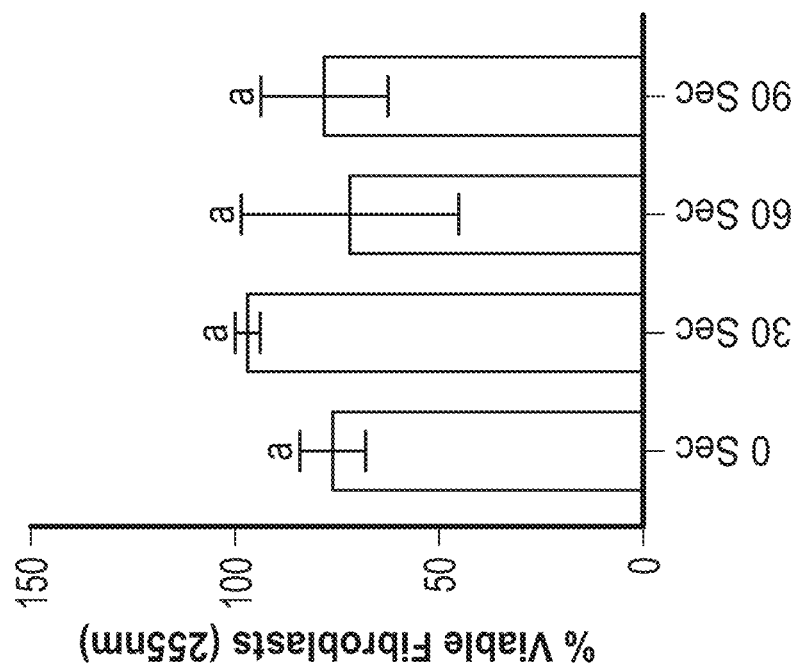
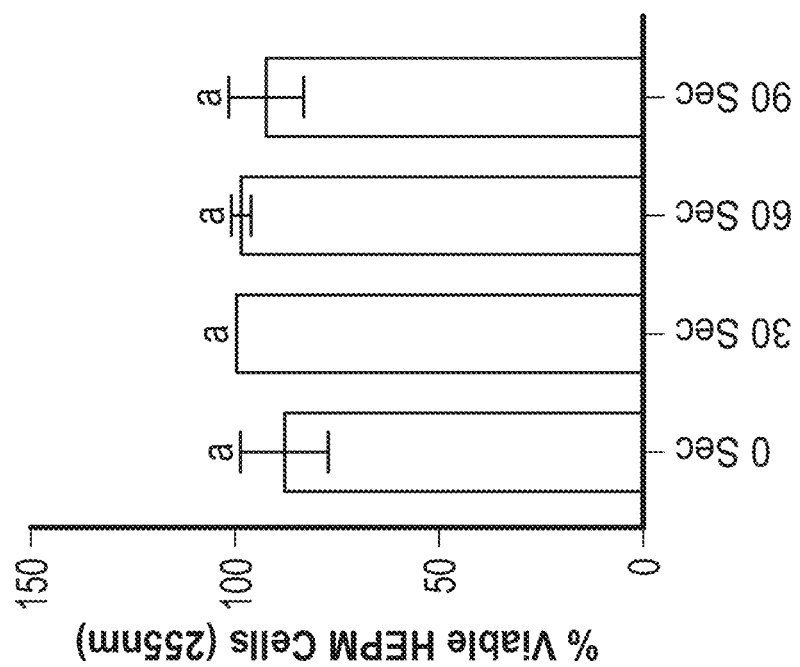
FIG. 14A
FIG. 14B

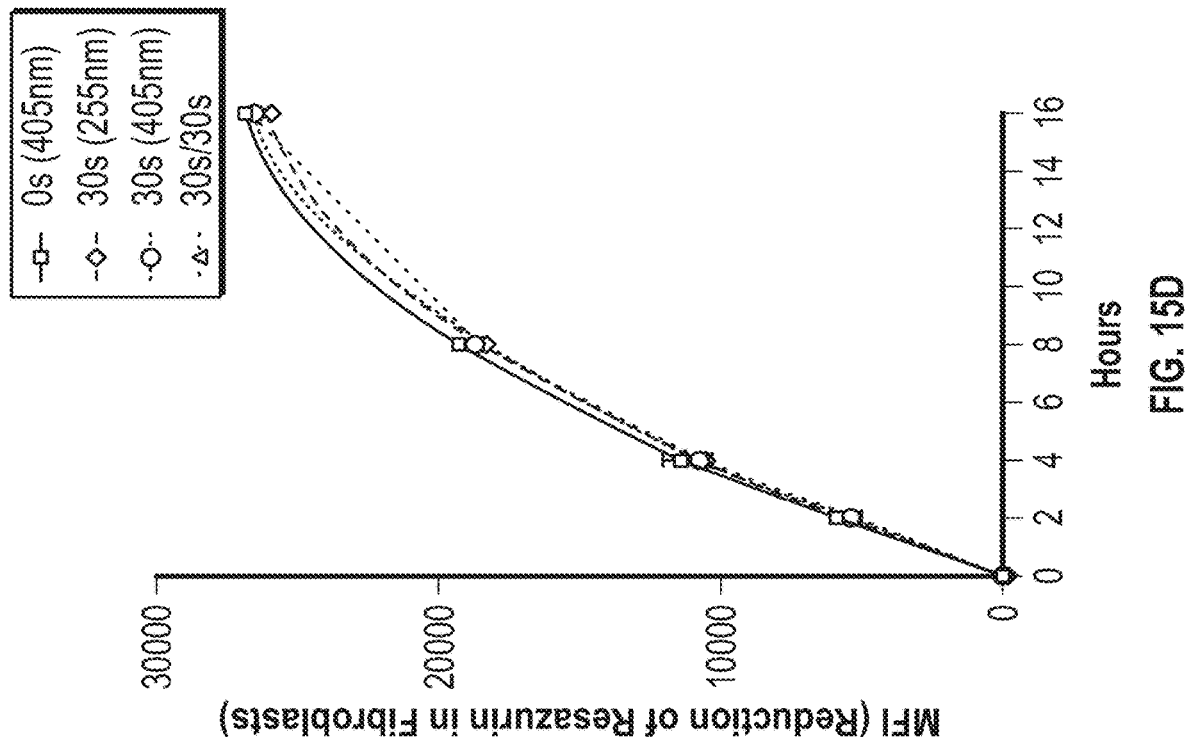
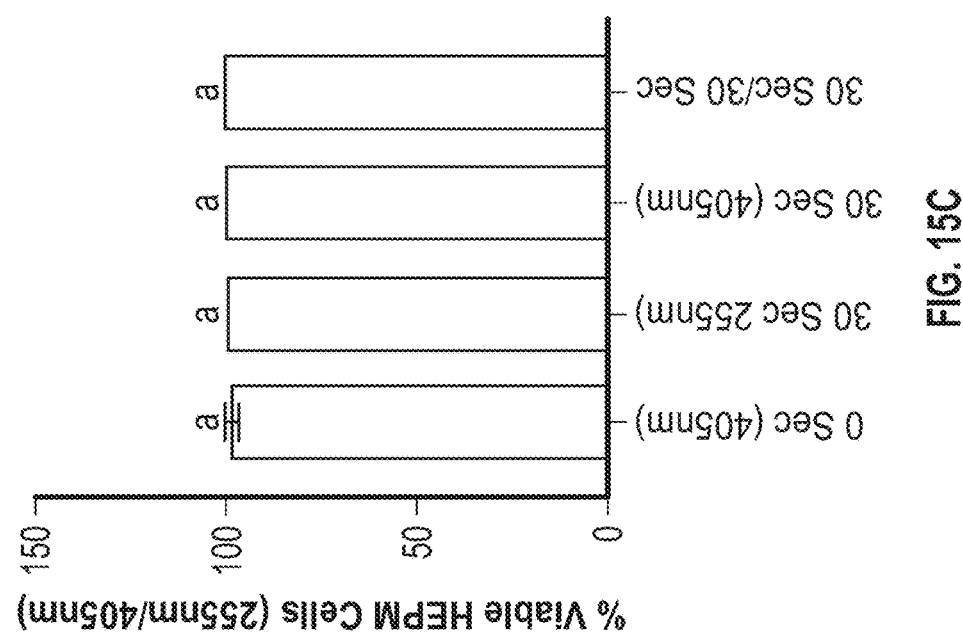

LIGHT BASED DENTAL TREATMENT DEVICE

CLAIM OF PRIORITY

This patent application claims the benefit of priority to U.S. Provisional Application Ser. No. 62/751,440, filed Oct. 26, 2018, which is incorporated by reference herein in its entirety.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever. The following notice applies to the software and data as described below and in the drawings that form a part of this document: Copyright University of Iowa Research Foundation, Iowa City, Iowa. All Rights Reserved.

TECHNICAL FIELD

This document pertains generally, but not by way of limitation, to treatments and instruments for treating microorganisms within and around the oral cavity and within and around anatomical passages or cavities.

BACKGROUND

Endodontic treatment includes, in part, bacterial disinfection of a root-canal system and the prevention of re-infection. In some examples, endodontic treatment involves chemical and mechanical debridement of the canal space for disinfection. Chemical irrigation infiltrates the root-canal system, and disinfects or dissolves tissue and removes necrotic debris from the canal wall.

For instance, irrigation of the canal system after mechanical formation of a passage removes tissue remnants, microorganisms and dentin chips by a continual flushing of the canal space. A combination of irrigants in sequence is optionally used for treatment. On example of an irrigant includes sodium hypochlorite (NaOCl) for its efficacy for disinfection and ability to dissolve organic material. In other examples, sodium hypochlorite is used in combination with Ethylenediaminetetraacetic acid (EDTA). The addition of chlorhexidine (CHX) as an irrigant is also used in some example because of its antimicrobial activity, for instance against *Enterococcus faecalis* (*E. faecalis*).

OVERVIEW

The present inventors have recognized, among other things, that a problem to be solved includes enhancing the disinfection of the canal system (or other anatomical passage or cavity). The instrumentation of the canal space is a step in the process of cleaning and disinfection. Mechanical instruments have limitations due to the complexity of the canal systems (e.g., lateral canals, fins and crevices along canal walls or the like). This has been demonstrated by microcomputed tomography (CT) scanning which showed large areas of the root canal walls that were left untouched by instruments. The instruments have limited ability to navigate the canal space and reach tissue remnants, microorganisms and dentin chips retained in these tortuous spaces. Accordingly, the clinician is reliant on the chemical irrigation of the canal system to disinfect the untouched canal features and achieve a successful outcome. However, chemical irrigants are also subject to the tomography of the canal (e.g., lateral canal passages, crevices, fins or the like) and in some examples fail to disinfect features of the canal. For instance, the flushed chemical irrigants fail to adequately reach tortuously hidden features along or extending from the canal. Additionally, remnant tissues, microorganisms or the like are, in some examples, suspended in or concealed by biofilms, collections of proteins, carbohydrates or the like that further complicate access by irrigants.

The present subject matter helps provide a solution to this problem, such as with a light-based dental treatment system configured to broadcast one or more wavelengths of therapeutic light within a cavity or passage of the tooth or other treatment location including, but not limited to, implants (treatment for prevention of acute peri-implantitis), periodontics (periodontal disease), possible operative (treatment of caries). The delivered therapeutic light achieves one or more therapeutic benefits (e.g., disinfection, tissue regeneration, revascularization of tissue, reduction of inflammation or pain or the like). The light-based dental treatment system includes a handle generator and one or more selectively coupled delivery shaft assemblies aligned and retained to the handle generator. The delivery shaft assemblies include profiles, such as distal shaft profiles (e.g., shapes, sizes, angles or the like) to facilitates access to a passage in the tooth or other treatment location through manipulation and application of the system within the oral cavity.

The light-based dental treatment device further includes at least one light delivery port along the instrument shaft, for instance a distal light port. Optionally, the device includes a plurality of light delivery ports configured to broadcast light in one or more directions including laterally, distally or the like and accordingly reach complex features found in and around the treatment location. The delivery shaft of the assembly further includes a reflective inner wall, fiberoptic element or the like that extends through the shaft to the at least one delivery port. A light element (e.g., an LED, laser diode, laser, quantum cascade laser or the like) remote from the at least one delivery port is in communication with the light passage and is configured to broadcast therapeutic light at one or more wavelengths. The delivery shaft conveys light to the at least one delivery port for delivery to the treatment location. In some examples, the distal shaft profile includes a varied profile relative to a proximal (base) shaft profile of the delivery shaft. The varied distal shaft profile delivers the therapeutic light to treatment locations in difficult to access regions of the oral cavity, locations having different shapes or sizes or the like.

The therapeutic light is broadcast into the cavity or passage and reaches the specified targets (tissues, microorganisms or the like) even in difficult to reach locations (lateral canals, fins and crevices along canal walls, and within biofilms, collections of proteins, carbohydrates or the like). Additionally, manipulation of the device including translation into and out of the tooth, rotation or the like increases the coverage of the one or more light delivery ports by moving the ports across arcs, along linear routes or the like. Further, by using one or more wavelengths of light a variety of microorganisms are killed to enhance the disinfection of the cavity or passage in the tooth.

This overview is intended to provide an overview of subject matter of the present patent application. It is not intended to provide an exclusive or exhaustive explanation of the disclosure. The detailed description is included to provide further information about the present patent application.

BRIEF DESCRIPTION OF THE DRAWINGS

FIG. 8 illustrates, by way of example, a diagram of an embodiment of an antimicrobial or tissue regeneration device.

FIG. 9 illustrates, by way of example, a diagram of an embodiment of an antimicrobial or tissue regeneration device.

FIG. 13A illustrates MFI vs time for human embryonic palatal mesenchyme (HEPM) cells after 255 nm treatment.

FIG. 13B illustrates MFI vs time for fibroblasts after 255 nm treatment.

FIG. 13C illustrates MFI vs time for HEPM cells after 405 nm treatment.

FIG. 13D illustrates MFI vs time for fibroblasts after 405 nm treatment.

FIG. 14A illustrates % of viable HEPM cells vs time after 255 nm treatment.

FIG. 14B illustrates % of viable fibroblasts vs time after 255 nm treatment.

FIG. 15C illustrates % of viable HEPM cells vs time after combination treatment with 255 nm and 405 nm wavelength electromagnetic energy.

FIG. 15D illustrates MFI vs time for fibroblast cells after combination treatment with 255 nm and 405 nm wavelength electromagnetic energy.

DETAILED DESCRIPTION

Figure 1:
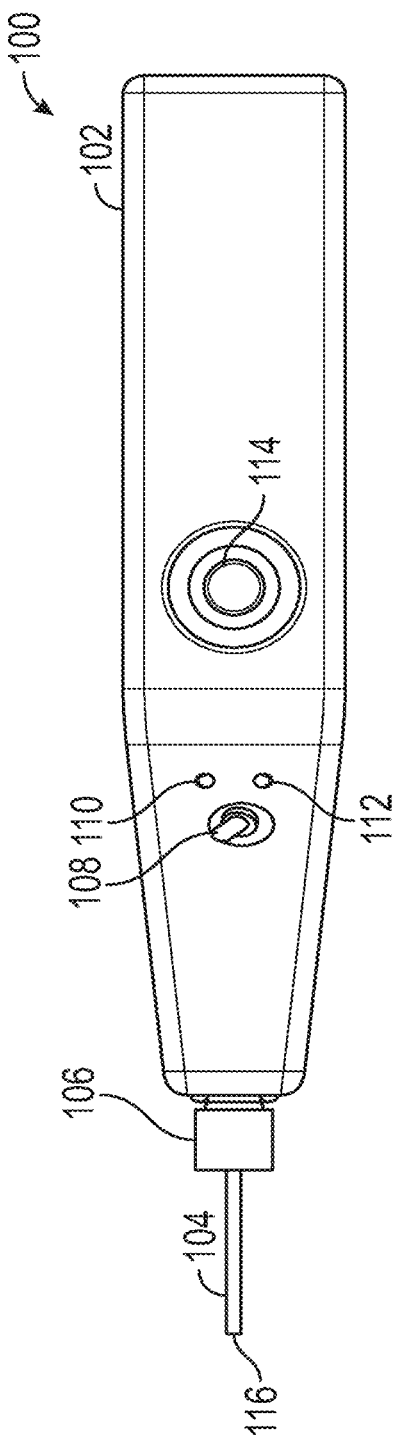
FIG. 1 illustrates, by way of example, a perspective view diagram of an embodiment of an electromagnetic energy-based tissue treatment system.

Embodiments regard selective sterilization of tissue using electromagnetic energy. The electromagnetic energy acts as a germicide. Infected or inflamed tissues (e.g., endodontic tissues or other internal tissues) can be treated using a chemo-mechanical debridement of canal spaces and closure of a canal opening. Some methods are available to further sterilize infected areas or initiate regeneration of local tissues. Embodiments regard light emitting diode (LED) treatment (e.g., at a specific wavelength 255 nm and 405 nm, among others) for the sterilization of internal tissues and the production of biomarkers related to tissue regeneration.

Antimicrobial effects of LED treatments on cultures of *E. faecalis* (*E. faecalis*) and the effects of LED treatment, in combination, on the production of osteoinductive, angiogenic, proliferative, and proinflammatory biomarkers from LED-treated HEPM cells and primary human gingival fibroblasts were determined. The LED treatment reduced the viability of *E. faecalis*. The LED treatment did not appreciably affect the viability of HEPM cells and human primary fibroblasts. The LED treatment at a first wavelength, alone or in combination with LED treatment at a second wavelength, of HEPM cells and human primary fibroblasts induced the production of biomarkers related to endodontic tissue regeneration. Embodiments provide a new treatment modality for the sterilization and regeneration of inflamed endodontic tissues using short periods of LED treatment.

Embodiments provide a new approach for disinfection of infected canals, especially the apical third of a canal (the deepest part of the infected tissue) that is likely not receiving a full effect of a chemical debridement (6% bleach solution). This solution (6% bleach) is quite caustic if expressed past the canal of a tooth. Embodiments show that there is a synergistic approach between an irrigation solution to tissue disinfection and a light source treatment (the LED treatment). Embodiments indicate that future disinfection of the infected tissue can be accomplished with a lower concentration bleach solution with decreased risk to patients. Embodiments have been assessed with infected root canals. However, the devices and methods described herein include potential benefits throughout dental, medical, and perhaps industrial applications (e.g., food preparation, conditioning, sterilization or the like). The devices and methods described herein have shown positive results for bactericidal benefits (anti-microbial) and have also initiated the production of markers indicating proliferation (tissue regeneration).

Embodiments regard devices and methods for precisely applying electromagnetic energy for invasive disinfection (or potential regeneration) of a target volume of tissue. In some embodiments, these devices and methods are applied to a patient, such as a human being or other living organism, through an open incision, opening or the like. A delivery shaft assembly emits electromagnetic energy generated by a light element (or other electromagnetic energy generation element) of one or more specified wavelengths into/onto a targeted volume of tissue to reduce infectious tissue volume and prohibit the tissue from proliferating or to destroy existing infectious tissue. In some embodiments, application of 253 nanometer (nm) wavelength energy is used. Energy of this wavelength is sometimes called "germicidal ultraviolet light". This specified wavelength has been proven to kill some bacteria. The effectiveness of the disclosed devices and methods can be a function of the amount of electromagnetic energy applied and the duration of application (e.g., the "time power product"). Embodiments regard application of electromagnetic energy to the target tissue both to prevent collateral damage to normal tissue, while also optimizing the efficiency of the claimed method. In the example application of 253 nm wavelength energy (known for deleterious effects on bacteria) a precision applicator is used. The precision applicator includes a delivery shaft selectively coupled (e.g., based on profile of the patient opening, positioning of the opening or the like) with a handle generator including the electromagnetic generating element. The disclosed devices can be used to apply the electromagnetic energy to infected tissue, through an incision or other opening in the subject. Further, the devices are equally effective when applied to a surface of a body of tissue (e.g., an abrasion or the like that is not internal to a patient).

Figure 2:
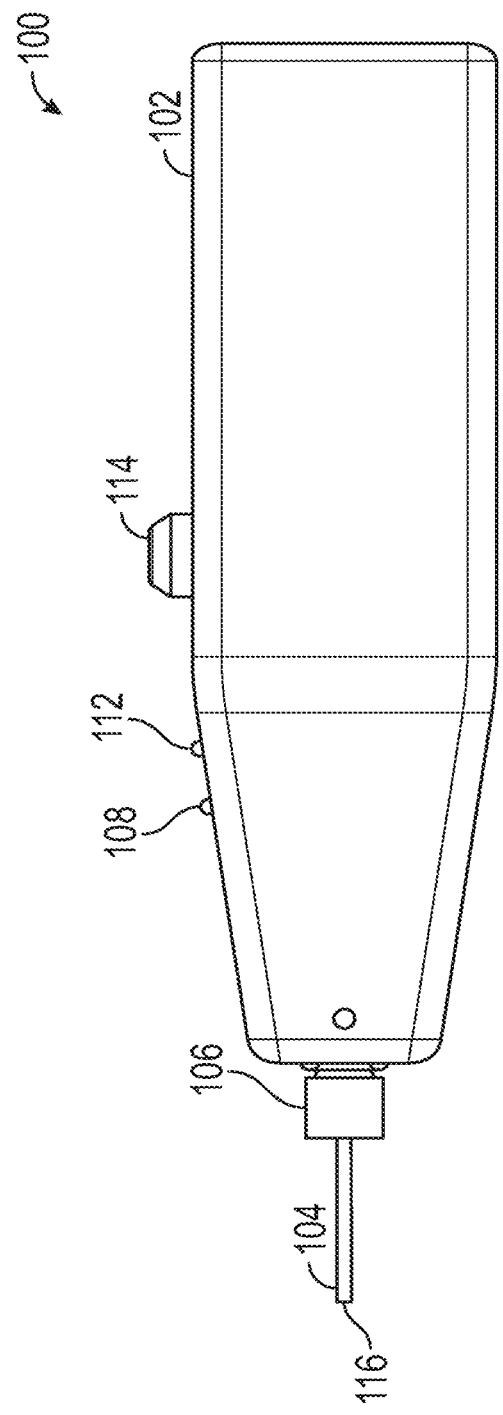
FIG. 2 illustrates, by way of example, another perspective view diagram of an embodiment of the electromagnetic energy-based tissue treatment system.

FIG. 1 illustrates, by way of example, a perspective view diagram of an embodiment of an electromagnetic energy-based tissue treatment system 100. FIG. 2 illustrates, by way of example, another perspective view diagram of an embodiment of the electromagnetic energy-based tissue treatment system 100. The perspective of FIG. 2 is from a direction indicated by arrows labelled "2" in FIG. 1. The system 100 as illustrated includes a generator housing 102, an electromagnetic energy delivery shaft assembly 104, an alignment collet 106, a power toggle 108, indicator elements 110, 112, and an electromagnetic energy delivery trigger 114.

The generator housing 102 provides an enclosure for circuitry. The circuitry is configured to control operations of the tissue treatment system 100. The generator housing 102 is used by tissue treatment personnel as a handle. The generator housing 102 is thus made of an electrically insulating material (a dielectric) in some embodiments. The generator housing 102 is made of one or more of a variety of materials, such as metal, ceramic, polymer, or the like, in some embodiments. The generator housing 102 is an elongate structure configured to fit comfortably in a palm of a hand.

The delivery shaft assembly 104 guides electromagnetic energy to a distal electromagnetic energy delivery port 116 thereof. The delivery port 116, in embodiments, includes one or more component delivery ports. Electromagnetic energy received at the delivery port 116 can be directed in a distributed manner to the component delivery ports (e.g., broadcast, sprayed, scattered, directed along one or more specified vectors, or the like). The delivery shaft assembly 104 includes a proximal electromagnetic energy port (shown in FIG. 3 among other FIGS.) to receive electromagnetic energy from an electromagnetic energy element of circuitry in the generator housing 102. The electromagnetic energy travels out the distal electromagnetic energy delivery port 116 of the delivery shaft assembly 104 to a therapy target. The delivery shaft assembly 104 thus provides a path for electromagnetic energy to travel from the circuitry in the generator housing 102 to a therapy target. The delivery shaft assembly 104 includes a variety of profiles (e.g., shapes or sizes) in differing embodiments. The different profiles include respective different bends (at different angles) along a length of the delivery shaft assembly 104, lengths, widths (e.g., diameters), or perimeters of the shaft assemblies 104, or the like. The different bends provide access to different internal tissues, cavities, or other targets. Examples of delivery shaft assemblies 104 are provided in FIG. 6

The alignment collet 106 retains the delivery shaft assembly 104 to the generator housing 102. Further, the alignment collet 106 aligns the proximal electromagnetic energy port of the delivery shaft assembly 104 with the electromagnetic energy port of the circuitry of the generator housing 102. A collet is a type of chuck, clamp, fitting, grip, collar, or the like that surrounds at least a portion of the delivery shaft assembly 104 and applies a clamping force to ensure alignment of a generator component 220 and a light port with tightening of the collet 106. The collet 106, in some embodiments, is squeezed against a matching taper of the delivery shaft assembly 106 and the inner surface of the collet 106 contracts to a smaller diameter, clamping the delivery shaft assembly 104 to hold it securely.

Figure 4:
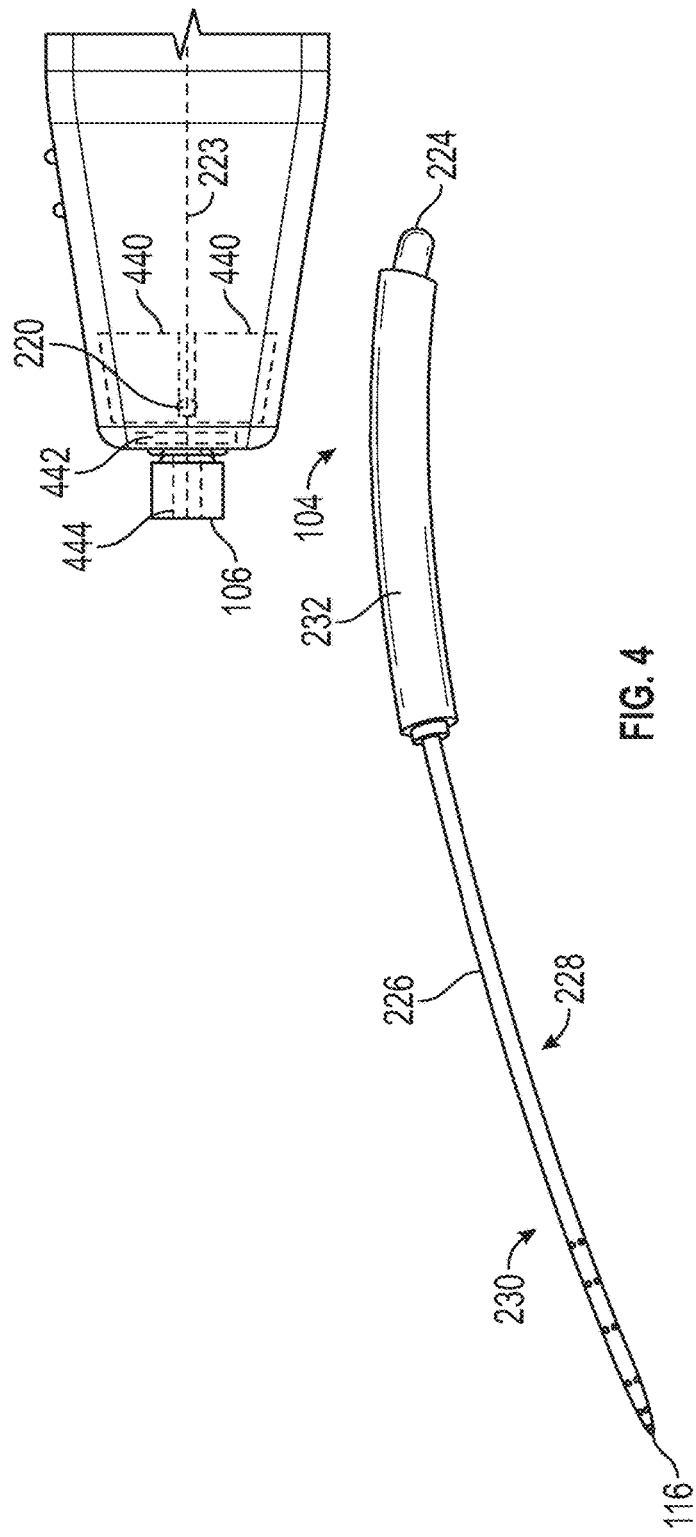
FIG. 4 illustrates, by way of example, a perspective view diagram of another embodiment of a system for bactericide and regeneration (healing) of tissue.

The alignment collet 106, in some embodiments, includes an interior collet profile complementary to a shaft profile of a shaft fitting 232 of the delivery shaft assembly 104 (see FIG. 4 for example). The alignment collet 106 applies opposing biases to the shaft fitting 232 to fix the delivery shaft 104 to the generator housing 102. The alignment collet 106 aligns the proximal light port 224 with the light element axis 222 of the energy generator component 220 (sometimes called a "light element"). The alignment with the light element axis 222 causes the light to be transmitted through the proximal light port 224, a delivery shaft 226, and out the distal light port 116 to a proximate structure (a therapy target).

The power toggle 108 is electrically coupled to a battery or other power source of the system 100. The power toggle 108 is a switch, button, pin or the like that opens or closes an electrical path between the circuitry of the generator housing 102 and the power source. In some embodiments, the power toggle 108 includes a push button, toggle, single pull single throw, single pull double throw, or other switch. A user operates the power toggle 108 to open or close the electrical coupling between the circuitry and the power source, thus providing electrical power to, or cutting off power to the circuitry.

The indicator elements 110, 112 provides one or more of a visible, audible, tactile indication of electrical power to the circuitry or delivery of the electromagnetic energy by the system 100. The indicator elements 110, 112 include, but are not limited to, a light source (e.g., an LED or other optical device), a speaker, a motor, a mechanism, or the like. In some embodiments one of the indicator elements 110, 112 indicate whether electrical power is provided to circuitry of the system 100 and another of the indicator elements 110, 112 indicates whether the system 100 is delivering electromagnetic energy.

The delivery trigger 114, in some embodiments, includes one or more of a switch, button, pin, or the like similar to the power toggle 108. The delivery trigger 114 operates to close or open an electrical path between the delivery shaft assembly 104 and an electromagnetic energy generation component of the circuitry or alternatively power (as another toggle) the electromagnetic energy generation component (e.g., after powering on of the system 100 with the power toggle 108).

In operation, a delivery shaft assembly 104 is attached to the system 100 by inserting the delivery shaft assembly 104 into the alignment collet 106 and tightening the alignment collet 106 around the delivery shaft assembly 104. The alignment collet 106 retains and aligns the delivery shaft assembly 104 with the electromagnetic energy port of the generator housing. The user then activates the circuitry using the power toggle 108 (e.g., powers on the system 100). The indicator element 110, 112 indicates that the circuitry is activated in response to the user activating the power toggle 108. The electromagnetic energy component of the circuitry is activated with the delivery trigger 114. Another, or the same, indicator element 110, 112 indicates that the electromagnetic energy component is activated in response to the user activating the delivery trigger 114. The energy generator component of the circuitry produces electromagnetic energy and delivers the energy the delivery shaft assembly 104 via the electromagnetic energy port of the generator housing 102. The electromagnetic energy is guided by the delivery shaft assembly 104 to the therapy target (e.g., through the delivery port 116).

Figure 3:
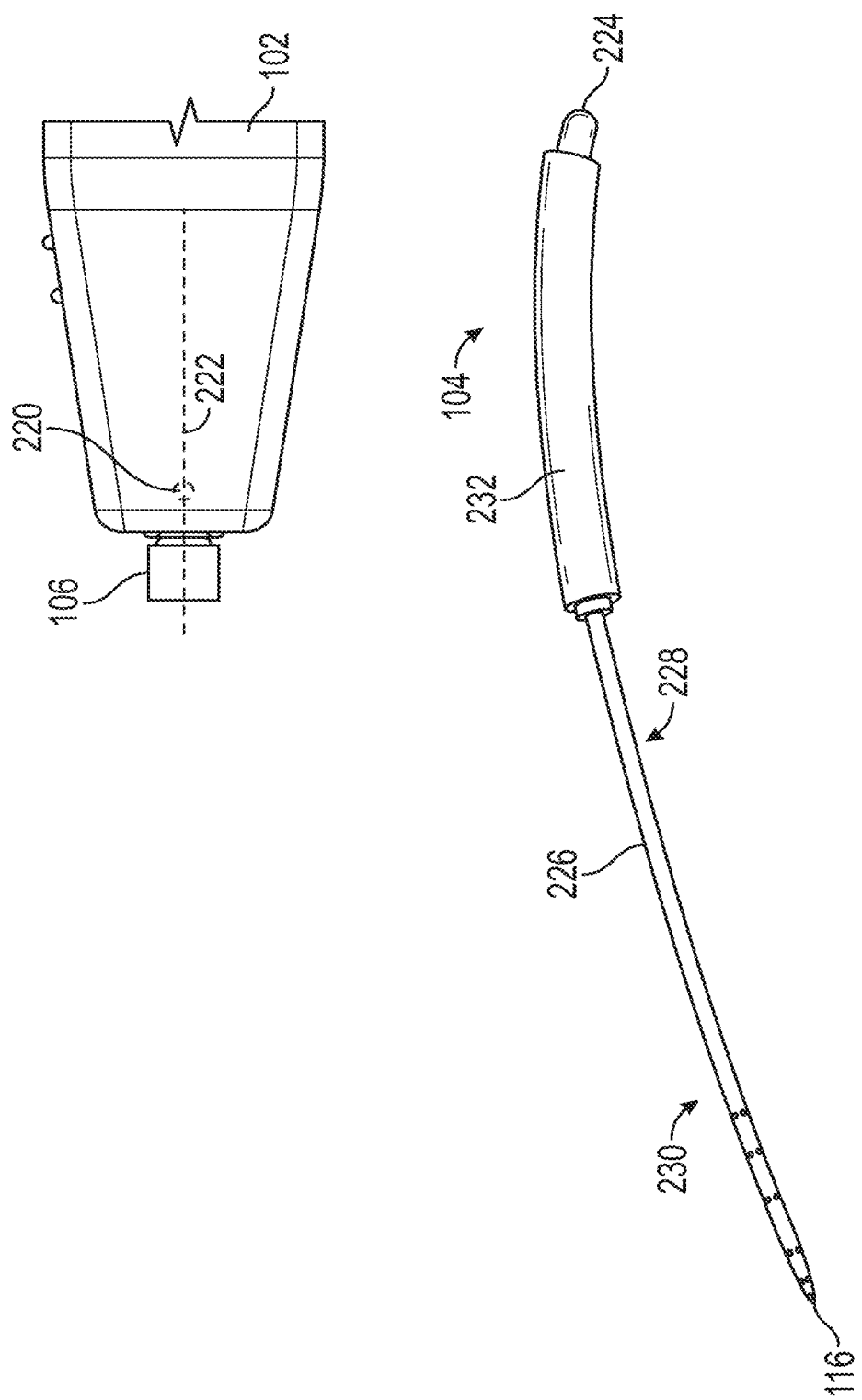
FIG. 3 illustrates, by way of example, another perspective view diagram of an embodiment of a light-based dental treatment system.

FIG. 3 illustrates, by way of example, another perspective view diagram of an embodiment of a light-based dental treatment system. In FIG. 3, the delivery shaft assembly 104 is disconnected from the generator housing 102. In FIG. 3, an energy generator component 220 is shown in dotted lines indicating that it is in the generator housing 102. The shaft assembly 104 illustrated in FIG. 3 is one example of one size and shape (collectively a profile) of the components of the shaft assembly 104. Additional examples of shaft assemblies are provided in FIG. 6.

The energy generator component 220 receives electrical energy and produces electromagnetic energy. The electromagnetic energy (in one example light or optical energy) is focused, such as by a waveguide, optical fiber, or the like, along a light element axis 222. The optical energy is provided to a proximal light port 224 of the delivery shaft assembly 104. An alignment of the proximal light port 224 and the energy generator component 220 is controlled by the alignment collet 106. The electromagnetic energy generator component 220 includes one or more visible light generating elements, non-visible light generating elements (e.g., that generate electromagnetic energy with wavelengths outside of visible light) combinations of the same or the like. For example, the energy generator component 220 includes, but is not limited to, an electronic oscillator circuitry, electrooptical lamps of various types, solid state electrooptical devices (lasers, LEDs, or the like).

The delivery shaft assembly 104, as illustrated, includes the proximal light port 224, the shaft fitting 232, the delivery shaft 226, and the distal light port 116. The proximal light port 224 receives electromagnetic energy from the energy generator component 220. The shaft fitting 232 is configured for reception and coupling with the generator housing 102 via the alignment collet 106. In some embodiments, the shaft fitting 232 includes a jacket that facilitates compressive gripping of the shaft assembly 104. The shaft fitting 232 minimizes (e.g., eliminates or minimizes) deformation of the shaft 226 of the shaft assembly 104. In some embodiments, the shaft fitting 232 includes a pliable material (including elastomeric, pliable, partially pliable or semi-pliable) that is readily grasped by the alignment collet 106. In some embodiments, the shaft fitting 232 includes a profile complementary to an interior profile of the alignment collet 106. The complementary profiles of the shaft fitting 232 and the alignment collet 106 enhances alignment of the proximal light port 224 with the energy generator component 220. Additionally, in other examples the complementary profiles of the shaft fitting 232 and the alignment collet 106 enhance retention of the shaft assembly 104 with the generator housing 102.

The delivery shaft 226, in some embodiments, includes a tubular element for transmitting the electromagnetic energy from the energy generator element 220 to the distal light port 116 of the shaft assembly 104. The delivery shaft 226, in some embodiments, includes one or more of a reflective hollow interior, solid fiber optic element, or the like.

The delivery shaft 226 includes a proximal shaft portion 228 that includes a proximal shaft profile and a distal shaft portion 230 that includes a distal shaft profile. The distal shaft portion 230 is distal to the proximal shaft portion 228. The proximal shaft portion 228 is proximate (and distal to) the shaft fitting 232. The proximal shaft portion 228 and the distal shaft portion 230 include respective profiles (e.g., sizes, shapes or the like) identical, similar or different from each other. In some embodiments, a cross-sectional area of the proximal shaft portion 228 perpendicular to the length of the shaft assembly 104 is smaller or larger than a cross-sectional area of the distal shaft portion 230 perpendicular to the length of the shaft assembly 104. In some embodiments, the shape (e.g., shape, angle, perimeter or the like) or size (e.g., length, width, diameter, or the like), collectively the profile, of either of the portions 228, 230 are varied to alter a energy transmission efficiency or a capability to provide electromagnetic energy to a specified therapy target.

The electromagnetic energy output of the energy generator component 220 is applied through a conduit (e.g., delivery shaft assembly 104), such as a modular delivery shaft coupled with the generator housing 102. The electromagnetic energy from the energy generator component 220 flows through the conduit to a target location (e.g., dental root, cavity, tissue or the like). The conduit focuses the emitted energy to the target location while minimizing dispersal around the energy generator component 220. One example of a conduit is a coaxial cable, through which radio energy flows. Another example of a conduit includes a light pipe, such as a fiberoptic element, coupled to an optical electrooptical generator. Light flows through the structure of the light pipe, and the light pipe channels and focuses the light and ensures emission from the distal light port of the lightpipe has a desired profile (delivery profile) according to the light pipe design (e.g., the porting, shape of the delivery shaft tip or the like).

Figure 16:
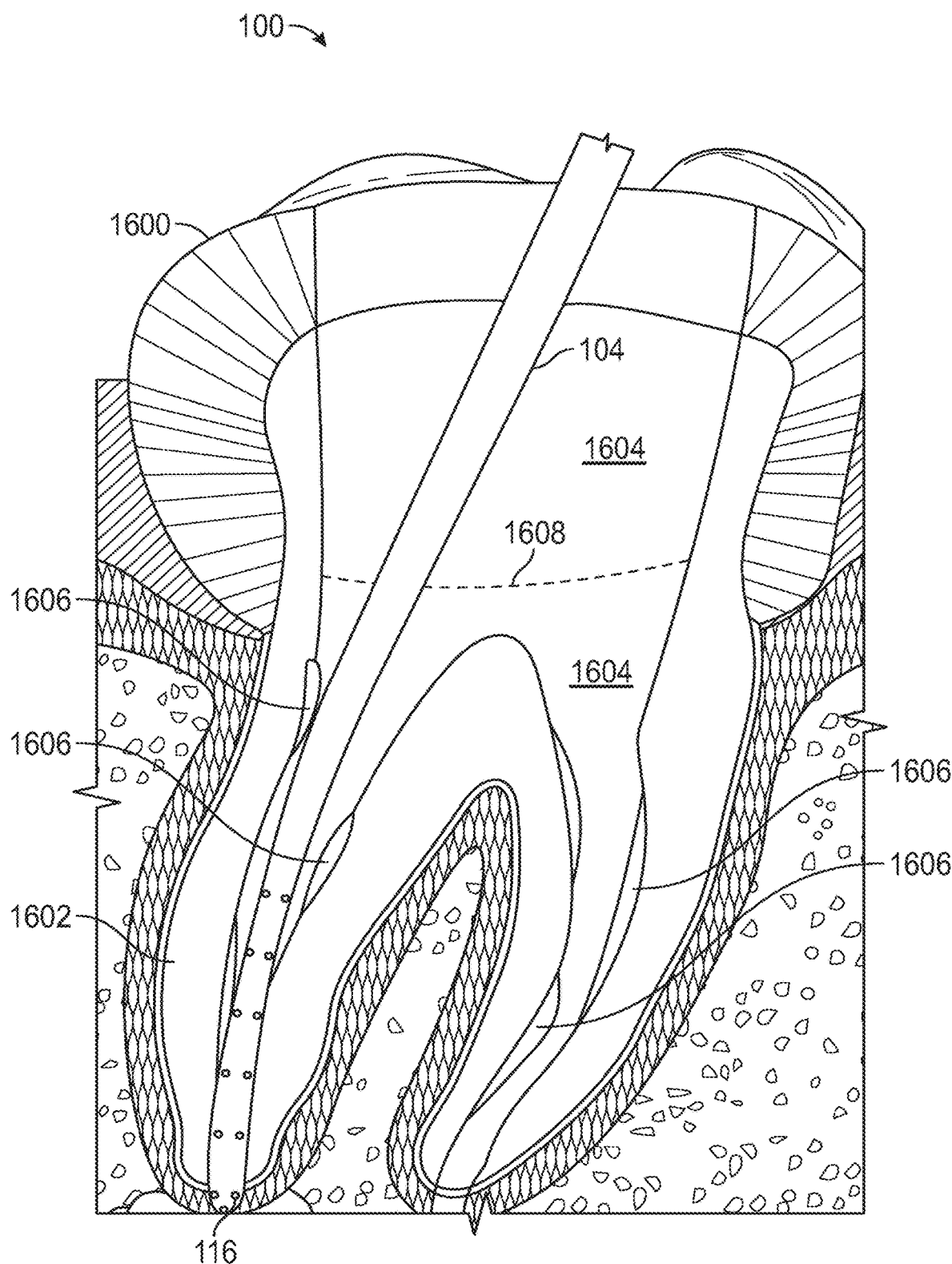
FIG. 16 shows one example of a tooth after mechanical removal of material (e.g., enamel, dentin, pulp or the like) to form one or more passages or cavities (treatment locations) within the tooth.

In various examples, the conduit, such as the delivery shaft 104, is inserted through an incision or opening to a target location, whether manually or under automated control. Optionally, insertion includes positioning of the distal light port 116 of the delivery shaft 236 to apply electromagnetic energy from the conduit to the target location (e.g., tissue or cavity). The electromagnetic energy, at a specified intensity, is applied to the target location for a specified duration shown to produce the desired effect on the target bacteria. The conduit, such as the distal light port 116, is stationary or moved during the application, depending on the desired coverage or effect. One example of delivery of the delivery shaft 104 is shown in FIG. 16 and includes the delivery shaft 104 navigated into a cavity formed in a tooth and ready for delivery of electromagnetic energy to a specified target location, in this example the interior of the root.

FIG. 4 illustrates, by way of example, a perspective view diagram of another embodiment of a system 400 for bactericide and regeneration (healing) of tissue. The system 400 is similar to the system 300, but includes additional components in the generator housing 102. The system 400 includes one or more heat sinks 440, a lens assembly 442, and an interior collet profile 444, in addition to items previously shown in FIGS. 1-3 and described herein.

The energy generator component 220 includes one or more LEDs (that operate to produce electromagnetic emissions of a same or different wavelength), laser light elements (that operate to produce electromagnetic emissions of a same or different wavelength), or the like. The wavelength or intensity of the electromagnetic energy provided by the energy generator component 220, in some embodiments, are variable and controlled by an intensity control or a frequency control (see FIG. 5). In some embodiments, the energy generator component 220 generates light with a wavelength between (and including) 200 nm to 405 nm. These wavelengths, when applied to (e.g., incident on) tissue, are antimicrobial and promote regeneration of the tissue. In some embodiments, the energy generator component 220 generates light with a wavelength between (and including) 255 nm to 280 nm. These wavelengths, when incident on tissue, are antimicrobial and promote regeneration of the tissue. In some embodiments, the energy generator component 220 generates light with a wavelength of about 265 nm.

The heat sink 440 conductively transfers heat away from the energy generator component 220, for instance through the proximate generator housing 102. The heat sink 440 includes metal, ceramic, or other material with a thermal conductivity configured to readily transfer heat away from the energy generator component 220. The heat sink 440, in some embodiments, includes one or more plates, fins, coils, tubes, posts, or the like, configured to transmit heat away from the energy generator component 220. As shown in FIG. 4 the heat sink 440 is coupled between the generator housing 102 and the energy generator component 220 and, in this example, conductively transfers heat from the energy generator component 220 to the generator housing 102.

The lens assembly 442 focuses electromagnetic energy toward the proximal light port 224 of the delivery shaft assembly 104. The lens assembly 442 includes one or more optical elements, such as a lens (convex or concave), a collimator, mirror, beam splitter, or the like. The optical elements are arranged to direct and focus the electromagnetic energy from the energy generator component 220 toward the proximal light port 224.

The interior collet profile 444 is interior to the alignment collet 106. The interior collet profile, in some embodiments, is complementary to a profile of the shaft fitting 232. In some embodiments, the interior collet profile 444 includes a tapered shaped that reduces width so that the delivery shaft assembly 104 has an interference fit thereto. The complementary profiles facilitate initial fitting of the delivery shaft assembly 104 and alignment with the energy generator component 220. The complementary profiles additionally aid retention of the delivery shaft assembly 104 to the generator housing 102. In some embodiments, one or more movable features (e.g., shoes, feet, rings, or the like) provide the interior collet profile 444. These features, in some embodiments, move relative to an uninterrupted passage extending from an end of the collet 106 to the lens assembly 442 or the energy generator component 220. Thus, movement of the movable features does not interrupt delivery of the electromagnetic energy from the energy generator component 220 to the shaft assembly 104.

In some embodiments, the shaft fitting 232 is integral to the shaft assembly 104. In other embodiments, the shaft fitting 232 is situated over the shaft assembly 104 and is manufactured as a separate part. In some embodiments, the shaft fitting includes a fitting profile complementary to the interior collet profile, such as to facilitate alignment between the collet 106 and the delivery shaft assembly 104 and retention of the delivery shaft assembly 104 to the collet 106. For example, the fitting profile and complementary profile include, but are not limited to, ovular, triangular, keyed, like sized circular profiles or the like.

Figure 5:
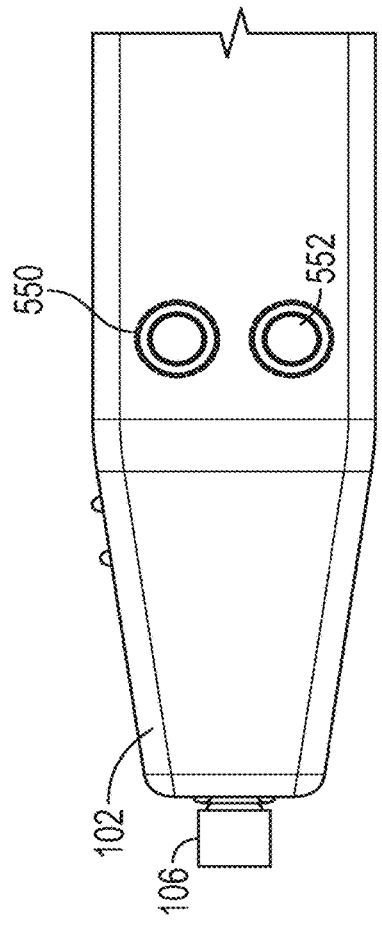
FIG. 5 illustrates, by way of example, a perspective view of a portion of the generator housing.

FIG. 5 illustrates, by way of example, a perspective view of a portion of the generator housing 102. The perspective of FIG. 5 provides an example of some components optionally proximal to the view provided in FIG. 4. As shown, the generator housing 102 includes an intensity control 550 and a frequency control 552.

The intensity control 550 includes a user input such as a knob, touch screen, dial, or the like, for adjusting the intensity of the electromagnetic energy generated by the energy generator component 220. The intensity is optionally graduated in terms of Joules, Joules per area, or the like. The intensity is adjusted (and optionally limited) to control the intensity of therapy delivered to the therapy target, enhance treatment efficacy and minimize (e.g., minimize or eliminate) potential harm at the therapy target. Optionally, if the intensity is increased (using the intensity control 550) the treatment time is in one example decreased and vice versa.

The frequency control 552 includes a user input such as a knob, touch screen, dial, or the like. In embodiments that include a touch screen, both of the frequency and the intensity are optionally controlled through the same touch screen. The frequency control 552 provides an adjustable control to vary the frequency of the electromagnetic energy generated by the energy generator component 220. In some examples, different frequencies of the delivered electromagnetic energy provide differing therapeutic benefits (or combinations of benefits) to the target area. For example, a first frequency includes enhanced antimicrobial effects (e.g., improved bactericidal properties) than a second frequency potentially having other therapeutic benefits (e.g., tissue regeneration, antimicrobial effect for a different bacteria or the like). In another example, a third frequency is better for regenerative effects than a fourth frequency.

Figure 6:
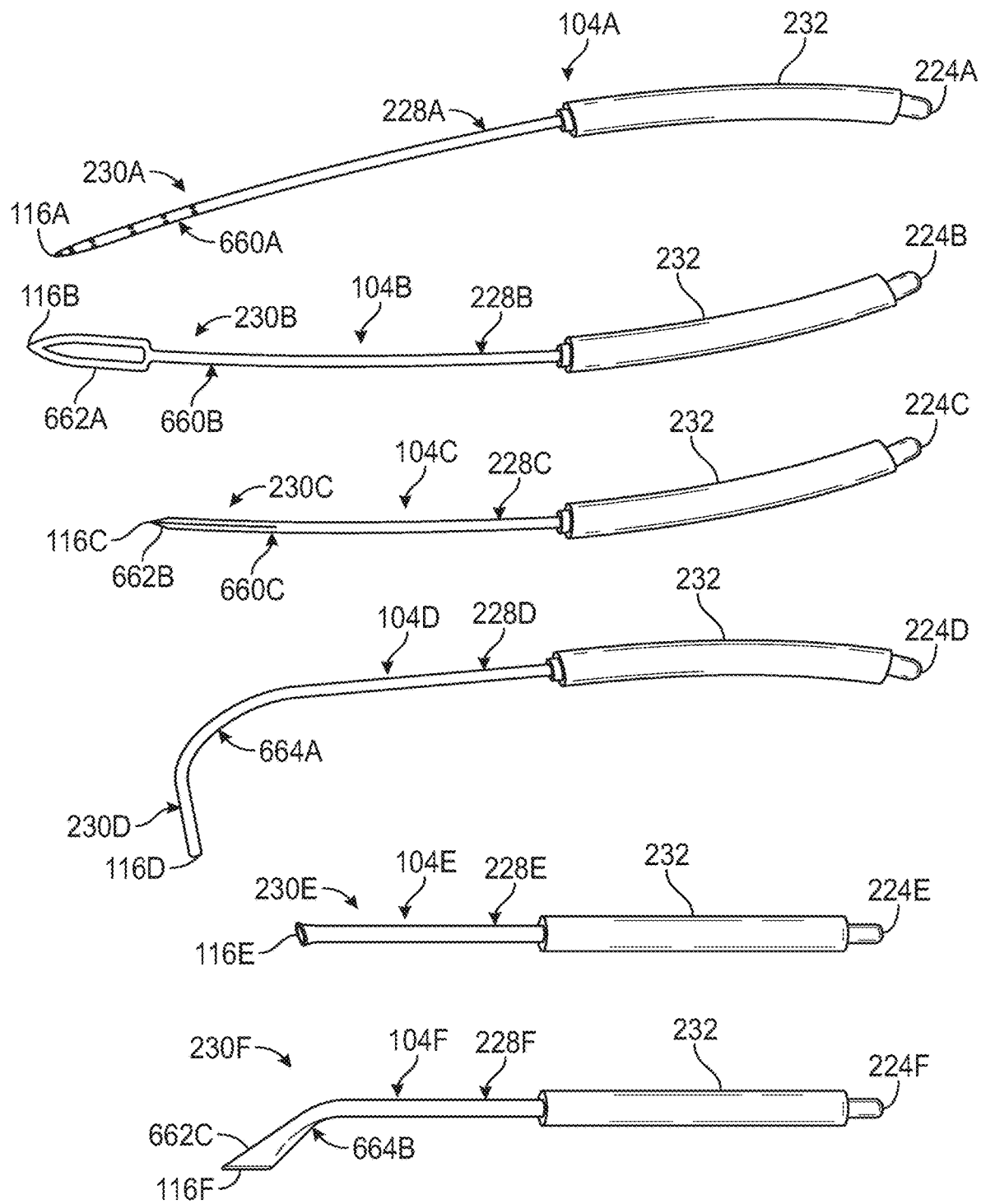
FIG. 6 illustrates, by way of example, a perspective view diagram of embodiments of delivery shaft assemblies.

FIG. 6 illustrates, by way of example, a perspective view diagram of embodiments of delivery shaft assemblies 104. Note that reference numbers with an alphabetic suffix are example embodiments of a component. Thus, each of delivery shaft assemblies 104A, 104B, 104C, 104D, 104E, 104F are example embodiments of the delivery shaft assembly 104, and each of distal shaft portions 230A, 230B, 230C, 230D, 230E, 230F are example embodiments of the distal shaft portion 230, and so on.

A previously discussed, the distal shaft portion 230, in various embodiments, is varied relative to the proximal shaft portion 228 of the delivery shaft assembly 104. Each of the distal shaft portions 230A-230F include different configurations relative to one another. For example, the different configurations include, but are not limited to, one or more of different tapers, lengths, widths, diameters, angles, bend angle at locations along the length of the assemblies, such as the distal shaft portions, or the like (collectively, profiles). In one example, the distal shaft portion 230A includes a greater length than the distal shaft portions 230C-230F. In another example, the distal shaft portion 230A further includes a narrow portion 660 relative to other portions of the distal shaft portion 230A. The narrow portion 660A (sometimes called a shaft joint) facilitates deflection of the distal light port 116A. The deflection of the distal light port 116A facilitates specified delivery of electromagnetic energy to a therapy target (e.g., navigated to the therapy target, guided to the therapy target, arranged for the delivery port 116 to be proximate the therapy target, or the like).

The distal shaft portion 230B includes a narrow portion 660B similar to the distal shaft portion 230A. The distal shaft portion 230B further includes a taper 662A (exaggerated for this illustration) proximate to the distal tip of the distal shaft portion 230A. The taper 662A facilitates access to a therapy target or enhances distribution of electromagnetic energy in a specified pattern (e.g., a specified spread, shape, arc, pattern, fan, angle or the like). The distal shaft portion 230B, similar to the distal shaft portion 230A, includes a greater length than the distal shaft portions 230C-230F.

The distal shaft portion 230C includes a length shorter than the distal shaft portions 230A-230B, but larger than the distal shaft portions 230D-230F. The distal shaft portion 230C includes a taper 662B in a most distal light portion thereof. The taper 662B is optionally less severe than the corresponding taper 662A of the distal shaft portion 230B, thus allowing the distal light port 116C access to different therapy targets than the distal light port 116B. For example, the taper 662A can facilitate delivery of electromagnetic energy to a like shaped cavity and tissues, while the taper 662B facilitates delivery of the electromagnetic energy to a narrower corresponding cavity.

The distal shaft portion 230D includes a bend angle that causes the delivery shaft assembly 104D to transmit electromagnetic energy generally perpendicular to a length of a proximal shaft portion 228D. The distal shaft portion 230D is shorter than the distal shaft portions 230A-230C and the distal shaft portions 230E-230F. The distal shaft portion 230D is generally uniform in width (e.g., diameter) along its length.

The distal shaft portion 230E is short and blunt. The distal shaft portion 230E is shorter than the other distal shaft portions 230A-230D and 230F shown in FIG. 6. The distal shaft portion 230E is generally uniform in width along its length, similar to the distal shaft portion 230D.

The distal shaft portion 230F includes a bend angle 664B that is smaller than the bend angle 664A of the distal shaft portion 230D. The distal shaft portion 230F further includes a taper 662C in a most distal light portion thereof. The taper 662C (or the tapers 662A-662B), in some embodiments, terminates in widths greater than, less than, or equal to a width of another portion of the distal shaft portion 230A-230F.

Each of proximal shaft portion 228A, 228B, 228C, 228D, 228E, 228F include generally uniform widths and varying lengths. However, the proximal shaft portions 228A-228F in other embodiments have a variety of lengths, widths, bends, tapers, angles, or the like.

The differing angles, tapers, bends, lengths, widths or the like of the distal shaft portions 230A-230F and the proximal shaft portions 228A-228F facilitate access to different treatment locations, features of treatment locations, or treatment locations having different features.

Each of the delivery shaft assemblies 104A-104F include a similar shaft fitting 232, however shaft fittings in different embodiments have different profiles, be made of different of materials, be manufactured separate from or integral to the delivery shaft assemblies 104A-104F. As previously discussed, the shaft fitting 232, in some embodiments, include a fitting profile (e.g., size or shape (e.g., circular, elliptical, ovular, triangular, rectangular, or the like) complementary to the interior collet profile 444. The interior collet profile 444 facilitates alignment and retention between the collet 106 and the proximal light port 224A, 224B, 224C, 224D, 224E, 224F. In some embodiments, the complementary fitting profile includes a keyed shape matched to a corresponding keyed shape of the interior collet profile 444.

Figure 7:
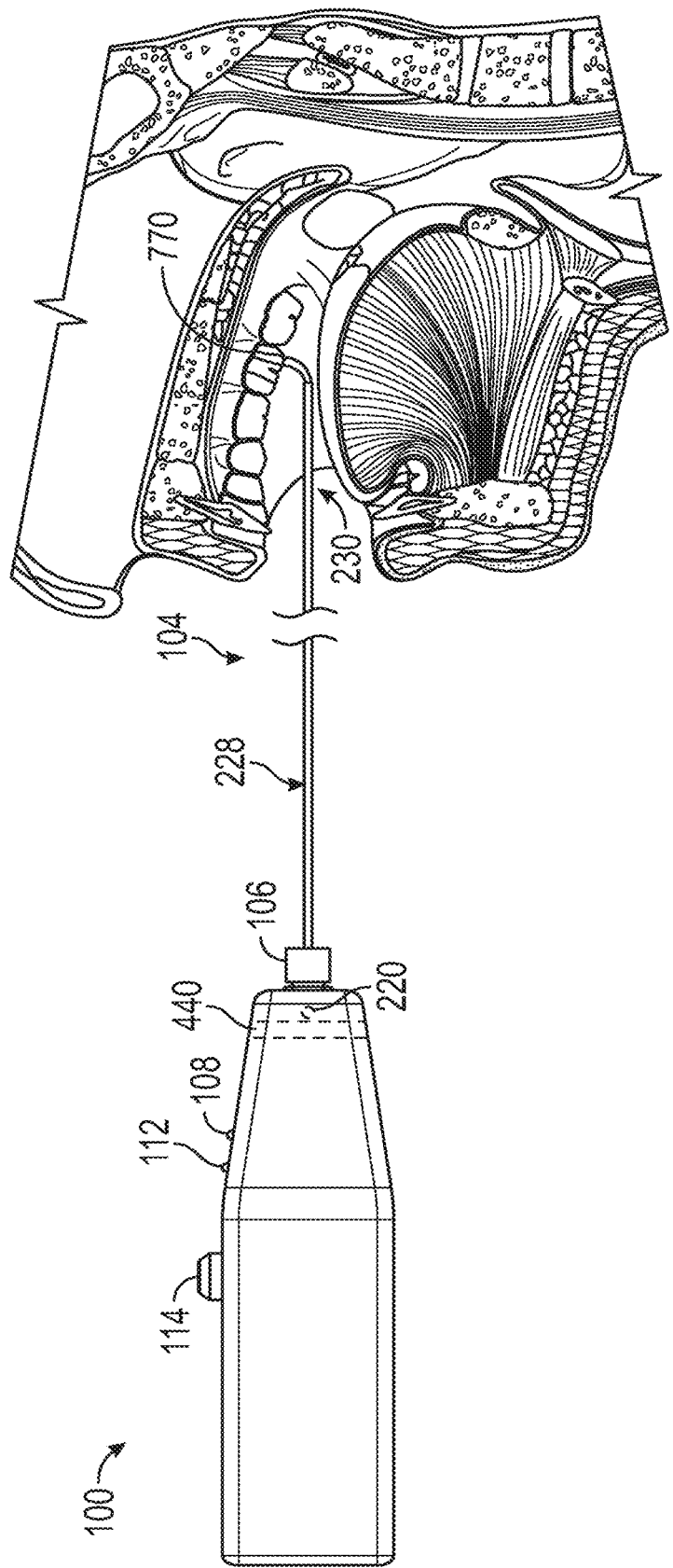
FIG. 7 illustrates, by way of example, a diagram of an embodiment of an antimicrobial and tissue regeneration system situated to provide electromagnetic energy to a therapy target.

FIG. 7 illustrates, by way of example, a diagram of an embodiment of an antimicrobial and tissue regeneration system 100 situated to provide electromagnetic energy to a therapy target 770. The system 100 and its components are discussed regarding FIGS. 1-6 and elsewhere herein. The heat sink 440 conducts heat away from the energy generator component 220 and to the generator housing 102. Positioning the energy generator component 220 outside of a body housing the therapy target 770 reduces an amount of heat conducted inside the body and allows the heat sink 440 to transfer the heat to atmosphere.

In the embodiment of FIG. 7, the therapy target 770 is an oral cavity (e.g., a recess for a root canal, a decay-based cavity, or the like). However, other infected, damaged, or other tissues that could benefit from antimicrobial or regenerative effects of embodiments are examples of therapy targets. The distal shaft portion 230 illustrated in FIG. 7 includes an angle and taper for accessing a vertically oriented cavity. In some embodiments, the delivery shaft assembly 104 is flexible, semi-rigid, rigid, or the like.

FIG. 8 illustrates, by way of example, a diagram of an embodiment of an antimicrobial or tissue regeneration device 800. The device 800 as illustrated includes components similar to the components of the system 100 discussed previously. The device 800 further includes circuitry in the generator housing 102 and an optional charging stand 886. The device 800 produces electromagnetic energy 880 for therapeutic effects on a therapy target. The circuitry of the device 800 illustrated includes a power source 884 and power converter circuitry 882. The power source 884, in some embodiments, includes an electrical power storage device, such as a battery, capacitor, or the like. In some embodiments, the power source 884 is a cord that can provide electrical power from an outlet to circuitry of the device 800. The power converter circuitry 882 can include an analog to digital converter, digital to analog converter, a voltage conditioner, a voltage or current regulator, or the like. The charging stand 886, in embodiments, is battery powered, plugged into an outlet, or the like. The charging stand 886 electrically charges the power source 884 so that the device 800 can be cordless during operation.

FIG. 9 illustrates, by way of example, a diagram of an embodiment of an antimicrobial or tissue regeneration device 900. The device 900 as illustrated includes components similar to the components of the system 100 discussed previously. The device 900 further includes circuitry mounted on a printed circuitry board (PCB) 990 in the generator housing 102. The circuitry on the PCB 990, in embodiments, includes the power converter circuitry 882, light element control circuitry (e.g., wavelength modulator, pulse modulator, therapy delivery time control circuitry (e.g., an oscillator, counter, or the like), or the like), the energy generator component 220, or other circuitry, such as a transistor, resistor, capacitor, multiplexer, processing device (e.g., an application specific integrated circuitry (ASIC), field programmable gate array (FPGA), central processing unit (CPU), graphics processing unit (GPU), or the like), diode, inductor, or the like, for operation of the device 900. In some embodiments, the PCB 990 includes a rigid or flexible substrate with traces or other electrically conductive elements (e.g., pads, vias, or the like) that provide electrical paths for electricity between components.

Figure 10:
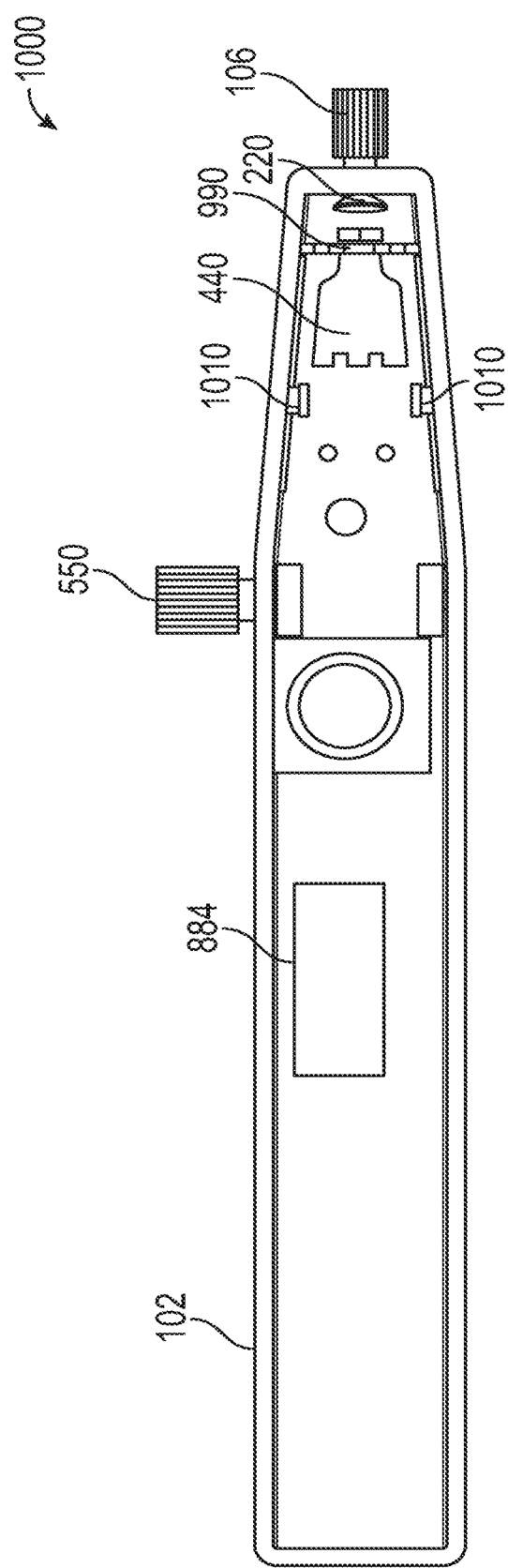
FIG. 10 illustrates, by way of example, a perspective view diagram of an embodiment of another light-based therapy system.

FIG. 10 illustrates, by way of example, a perspective view diagram of an embodiment of another light-based therapy system 1000. The system 1000 as illustrated includes components similar to the components of the system 100 discussed previously. The system 1000 further includes control contacts 1010. The control contacts 1010 complete or open an electrical path between the power source 884 and the energy generator component 220. The control contacts 1010, in embodiments, act as heat sinks to conduct thermal energy away from the energy generator component 220.

The devices described herein are contained in a handheld device that are battery, cord powered, or remotely powered implements. The handheld device is sometimes called a handle generator. The clinician or other personnel couples the delivery shaft assembly 104 to the handle generator housing 102 and align a proximal light port 236 of the delivery shaft assembly 104 with the energy generator component 220 (e.g., LED element, bulb, laser generator, oscillating circuit or the like). The clinician, or other personnel, operates a control to activate the energy generator component 220 and apply electromagnetic energy from the distal light port 116 of the delivery shaft assembly 104 to the therapy target 770. In another example, an onboard battery is exchanged for an umbilical cord to an external power source. In another example, the electromagnetic generator and power source are external to the patient, and accordingly heat generated by the generator is dissipated externally and safely away from the patient.

Figure 11:
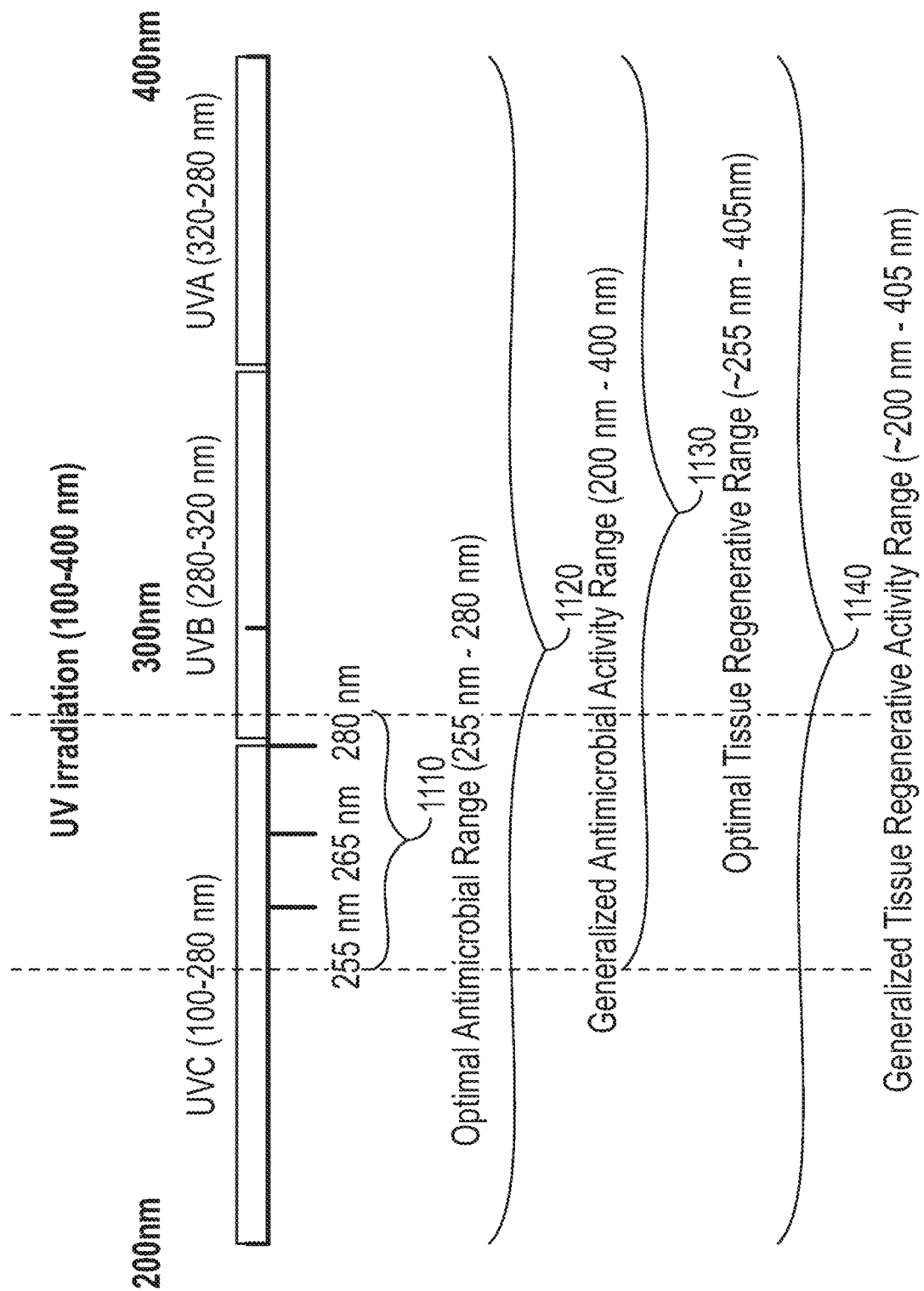
FIG. 11 illustrates, by way of example, a plot of an embodiment of wavelengths of electromagnetic energy for antimicrobial and tissue regeneration.

FIG. 11 illustrates, by way of example, a plot of an embodiment of wavelengths of electromagnetic energy for antimicrobial and tissue regeneration. In the plot, an optimal wavelength range for antimicrobial effects is provided at 1110, a generalized wavelength range for antimicrobial effects is provided at 1120, an optimal wavelength range for tissue regeneration is provided at 1130, and a generalized wavelength range for tissue regeneration is provided at 1140.

The optimal wavelength range for antimicrobial effects is about 255 nm to about 280 nm. The generalized wavelength range for antimicrobial effects is about 200 nm to about 400 nm. The optimal wavelength range for tissue regeneration is about 255 nm to about 405 nm. The generalized wavelength range for tissue regeneration is about 200 nm to about 450 nm. The optimal ranges for antimicrobial effects and tissue regeneration overlap in the 255 nm to about 280 nm wavelength range.

The electromagnetic energy output of the generator (e.g., a handle generator) is applied through a conduit, such as a modular delivery shaft coupled with the generator. The electromagnetic energy flows through the conduit to a target location (e.g., dental root, tissue or the like). The conduit focuses the emitted energy to the target location while minimizing dispersal around the generator. One example of a conduit is a coaxial cable, through which radio energy flows. Another example of a conduit includes a light pipe, such as a fiberoptic element, coupled to an optical electrooptical generator. Light flows through the structure of the light pipe, and the light pipe channels and focuses the light and ensures emission from the distal light port of the lightpipe in a desired profile (delivery profile) according to the light pipe design (e.g., the porting, shape of the delivery shaft tip or the like).

Testing Summaries

As previously discussed, successful treatment of infected or inflamed endodontic tissues can include chemo-mechanical debridement of the canal spaces and proper sealing of coronal and apical canal openings. Methods are available to further sterilize infected areas or initiate regeneration of local tissues. The ability of 255 nm and 405 nm light emitting diode (LED) treatment to kill *E. faecalis* and induce the production of cellular biomarkers related to endodontic tissue regeneration were assessed. The antimicrobial effects of 255 nm and 405 nm LED treatment on *E. faecalis* and the effects of 255 nm and 405 nm LED treatment on the production of osteoinductive, angiogenic, proliferative, and proinflammatory biomarkers from human embryonic palatal mesenchyme (HEPM) cells and gingival fibroblasts were assessed. It was observed that 1) at least 255 nm LED treatment killed *E. faecalis*, 2) 255 nm LED and NaClO efficiently killed *E. faecalis*, 3) neither 255 nm nor 405 nm LED treatment affected the viability of HEPM cells and gingival fibroblasts, and 4) 255 nm LED treatment, alone or in combination with 405 nm LED treatment, of HEPM cells and gingival fibroblasts induced the production of biomarkers related to endodontic tissue regeneration. The results suggest a new treatment modality using periods of 255 nm LED treatment as an adjunct to chemo-mechanical debridement for the sterilization of infected and inflamed sites and the production of biomarkers related to endodontic tissue regeneration. A few methods are available to sterilize infected canals or induce the production of biomarkers related to endodontic tissue regeneration. Treatment of canals with 255 nm light emitting diodes (LED) has the potential to sterilize infected and inflamed sites and induce the production of biomarkers related to endodontic tissue regeneration.

Successful treatment of infected or inflamed endodontic tissues can depend on disinfection of the root-canal system through chemo-mechanical debridement of the canal space and closure of the canal opening to prevent re-infection. Successful treatment is dependent upon i) bacterial disinfection of the root-canal system to prevent re-infection, and ii) chemical irrigation to disinfect, dissolve, and remove necrotic debris from the canal wall and spaces. The instrumentation of the canal space can be a step in these processes, but has limitations due to the complexity of the lateral canals, fins, and crevices along the walls of the canal systems. This has been demonstrated by microcomputed tomography (CT) scanning which showed extensive root canal configuration and large areas of the root canals walls that were left untouched by the instruments.

Light based technologies involving ultraviolet C (UVC, 200-280 nm) and blue light (400-450 nm) therapies offer attractive approaches as an adjunct to chemo-mechanical debridement for controlling microbial infections with beneficial impacts on local tissues. Both UVC and blue light are antimicrobial with relatively minor effects to host tissues compared to their high antimicrobial activity to microbial pathogens. Also attractive is the reported ability of laser irradiation to increase proliferation of mesenchymal cells, increase proliferation and mineralization of dental pulp constructs, increase cell proliferation and bone sialoprotein expression in dental pulp stem cells (DPSCs), and induce the production of TGF-$\beta$1, which is involved in differentiation of DPSCs.

*E. faecalis* induces persistent infections and is often associated with root canal infections and endodontic disease. In this study, the ability of 255 nm and 405 nm LED to kill *E. faecalis* was assessed. The effect of 255 nm and 405 nm LED on the viability of HEPM cells and gingival fibroblasts and the ability of 255 nm and 405 nm LED combination treatment of HEPM cells and gingival fibroblasts to induce the production of osteoinductive, angiogenic, proliferative, and proinflammatory biomarkers was also assessed.

*E. faecalis* was cultivated in BBL trypticase soy broth with 0.6% yeast extract and on trypticase soy broth, yeast extract containing Difco 1.5% agar at 37° C. Three hour bacterial cultures were adjusted in TSBYE broth to an optical density of 0.108 at 600 nm. Plate counts determined that these cultures contained $4.5-5.9 \times 10^7$ colony forming units (CFU) E. faecalis/ml.

For surface killing assays, a sterile swab was dipped into the adjusted culture and streaked onto a TSBYE agar plate to create a 'bacterial lawn' of confluent growth.

To determine the kinetics of antimicrobial activity, the adjusted culture was then diluted $10^{-3}$-fold to contain $\sim 10^5$ CFU/ml. 7.0 mm discs were punched from cellulose nitrate filter membranes (7182-002 plain cellulose nitrate filter membrane, 0.2 µm) and placed on TSBYE agar plates. 5 µl of microbial culture was added to each disc and incubated for 30 minutes.

To determine the synergistic effects of 255 nm LED and NaClO treatments, E. faecalis was diluted tenfold from $10^{-2}$-fold to contain $\sim 10^6$ colony forming units/ml.

Human embryonic palatal mesenchyme (HEPM) cells are pre-osteoblast cells and were obtained. These cells are responsive and have been used to i) study epigenetic regulation of osteogenesis and bone regeneration; evaluate craniofacial palatal closure; and study osteoblast growth, adhesion, spreading patterns, and differentiation. HEPM cells were cultivated in Dulbecco's Modified Eagle Medium (DMEM). The DMEM complete medium contained 1.0 g/L D-glucose, L-glutamine, 110 mg/L sodium pyruvate, 10.0% fetal bovine serum (No. 30-2020, ATCC), and 1% penicillin-streptomycin (No. 15140-122, Penicillin-Streptomycin, 10,000 U/ml). The identity of the HEPM cell line was authenticated by genetic profiling of their polymorphic short tandem repeat (STR) loci. Eight STR loci (TH01, TPOX, vWA, CSF1PO, D16S539, D7S820, D13S317 and D5S818) were examined for cell line authentication, and amelogenin was examined for gender identification and human cell line authentication. The STR profile results for the HEPM cell line used in this study were identical to the STR profile for the ATCC HEPM cell line.

Primary human gingival fibroblasts were also used and obtained. Gingival fibroblasts were cultivated in Fibroblast Basal Medium (ATCC PCS-201-030) with the added fibroblast growth kit (PCS-201-041) containing 0.5 ml/L rh FGFb (5 ng/ml); 18.75 ml/L L-glutamine (7.5 mM); 0.5 ml/L ascorbic acid (50 µg/ml); 0.5 ml/L hydrocortisone hemisuccinate (1 µg/ml); 0.5 ml/L recombinant human insulin (5 µg/ml) and 10.0% fetal bovine serum (No. 30-2020). These were primary cells and thus could not be authenticated.

Both HEPM cells and gingival fibroblasts were cultivated in T75 flasks at 37° C. in a humidified incubator with 5.0% $CO_2$. At ~70-80% confluent growth, cells were detached with 0.25% trypsin-0.53 mM EDTA solution, washed in their respective media, counted, and adjusted to contain $1.0 \times 10^5$ viable cells/ml. 200 µl aliquots were removed and put into 96-well microtiter plates. The plates were incubated for 16 hours in a humidified incubator at 37° C. with 5.0% $CO_2$.

255 nm and 405 nm LEDs were obtained. Wavelengths and energy dose were determined. The energy dose ($J/cm^2$) was calculated as the irradiance ($mW/cm^2$)×time (s). For 30 seconds, cells were exposed to 0.03 $J/cm^2$ (255 nm LED) and 0.00 $J/cm^2$ (405 nm LED).

LEDs were put into 3-dimensional printed holders, which served as a heat sink to prevent both LED and sample from heating during LED treatment. The LEDs were supported by clamps hooked to a ring stand above a scissors jack. An aluminum canula was placed into the LED source to direct LED light onto agar plates containing the cultures of E. faecalis and into the tissue culture wells of the 96-well plate containing HEPM cells and gingival fibroblasts.

To assess the effects of 255 nm and 405 nm LED treatments on E. faecalis viability, TSBYE agar plates were swabbed with E. faecalis and treated with 255 nm LED or 405 nm LED for 0, 30, 60, and 90 seconds. After treatment, the plates were incubated for 16 hours at 37° C. and examined for areas void of microbial growth. The surface of membrane discs containing E. faecalis were treated with 255 nm LED or 405 nm LED for 0, 30, 60, and 90 seconds. The discs were then removed from the agar surface, placed in 1.0 ml TSBYE broth, and mixed. 50 µl of each broth culture was put onto TSBYE agar plates in triplicate. Plates were incubated at 37° C. for 16 hours. Colonies per spot were counted, multiplied by 20 to get CFU/ml, and the percent killing was determined by comparing the concentrations of each treatment time point to the non-treatment time point control.

To assess the synergistic effects of 255 nm LED and sodium hypochlorite (NaClO) treatments on E. faecalis viability, 10 µl of a $10^{-2}$ bacterial dilution was put into holes (3 mm dia.) punched in blood agar plates containing trypticase soy agar with 5% defibrated sheep blood and incubated for 30 minutes to allow absorption of the culture media into the agar leaving E. faecalis on the walls of the wells. Each well was then administered a different treatment. One well was filled with 10 µl of distilled water and served as the untreated control. A second well was treated for 30 seconds with 255 nm LED. A third well was treated with 10 µl of 1% NaClO solution for 60 seconds. A fourth well was treated for 30 seconds with 255 nm LED and then 60 seconds with 10 µl 1% NaClO. A fifth well was treated for 60 seconds with 10 µl 1% NaClO and then for 30 seconds with 255 nm LED. After each treatment, wells were rinsed with 10 µl of TSBYE broth to remove bacteria and suspended into 1.0 ml of TSBYE broth. Each tube was mixed and 50 µl was removed and spotted on to blood agar in triplicate. Plates were incubated overnight at 37° C. with 5% $CO_2$ and colonies were counted the next day.

To assess the effects of 255 nm and 405 nm LED treatments on HEPM cell and gingival fibroblast metabolism (e.g., the conversion of resazurin to resorufin), 180 µl of tissue culture media was removed from the adherent cells leaving 20 µl of media in each well to prevent the cell monolayer from drying during treatment. HEPM cells and gingival fibroblasts were each treated with 255 nm LED for 0, 30, 60, and 90 seconds. HEPM cells and gingival fibroblasts in other wells were treated with 405 nm LED for 0, 30, 60, and 90 seconds. In additional experiments, HEPM cells and gingival fibroblasts were exposed to 255 nm LED for 30 seconds, 405 nm LED for 30 seconds, or a combination of 255 nm LED for 30 seconds followed by 405 nm LED for 30 seconds. After treatment, 200 µl of complete media with 1.0% Alamar Blue was added per well and the cells were incubated in a humidified incubator at 37° C. with 5.0% $CO_2$. Median fluorescence intensity (MFI) for the conversion of resazurin to resorufin was measured at 0, 2, 4, 8, and 16 hours post-LED treatment. WI of the metabolic reduction of resazurin to resorufin was determined using an excitation wavelength of 544 nm and an emission wavelength of 590 nm.

To assess the effects of 255 nm and 405 nm LED treatment on HEPM cell and fibroblast viability, 180 µl of tissue culture media was removed from the adherent cells in culture. HEPM cells and fibroblasts were each treated with 255 nm LED for 0, 30, 60, and 90 seconds. HEPM cells and fibroblasts in other wells were treated with 405 nm LED for 0, 30, 60, and 90 seconds. In additional experiments, HEPM cells and fibroblasts were exposed to 255 nm LED for 30 seconds, 405 nm LED for 30 seconds, and a combination of 255 nm LED for 30 seconds followed by 405 nm LED for 30 seconds. Immediately after treatment, 200 μl of the LIVE/DEAD working solution, containing 2 μM calcein AM and 4 μM ethidium homodimer-1 (EthD-1), was added per well and the cells were photographed. Calcein AM is a non-fluorescent compound that is converted to a green-fluorescent calcein by intracellular esterase activity in viable cells and EthD-1 is a weakly fluorescent compound until bound to DNA in non-viable cells. The plates were incubated for 45 minutes and read in the spectrophotometer. Calcein was excited at 485 nm and detected at 530 nm. EthD-1 was excited at 530 nm and detected at 645 nm.

To assess the effects of 255 nm and 405 nm LED treatment on the production of osteoinductive (BMP-2, BMP-4, BMP-9, and BMP-10), angiogenic (VEGFA, PDGF-A, FGF-acidic, and PIGF), proliferative (EGF and TGFα), and proinflammatory factors (IL6, IL8, and TNFα) from HEPM cells and fibroblasts, 180 μl of media was removed from the adherent cells in culture. HEPM cells and fibroblasts were each treated with 255 nm LED for 30 seconds, 405 nm LED for 30 seconds, and a combination of 255 nm LED for 30 seconds followed by 405 nm LED for 30 seconds. After treatment, 200 μl complete media was added to the plates containing HEPM cells and fibroblasts and incubated in a humidified incubator at 37° C. with 5.0% $CO_2$. Cell culture media was removed at 0, 24, and 48 hours post-LED treatment and frozen at −80° C. until analysis.

The concentrations of osteoinductive (BMP-2, BMP-4, BMP-9, and BMP-10), angiogenic (VEGFA, PDGF-A, FGF-acidic, and PIGF), proliferative (EGF and TGFα), and proinflammatory factors (IL6, IL8, and TNFα) in HEPM and fibroblast culture media were determined in triplicate wells using multiplex immunoassays (Luminex Human Magnetic Assay, R&D Systems, Minneapolis, MN) read on the Luminex100 (Luminex, Madison, WI). These immunoassay kits use antibody-coated magnetic beads to bind the desired analyte and use a standard curve of known concentrations to determine the unknown concentrations. Curves were constructed from the standards and their respective MFI readings and values were interpolated directly on the instrument and readout files.

To perform a statistical analysis, the MFI values and biomarker concentrations were first transformed by adding 1.0 MFI unit or 1.0 pg/ml to each respective value. A log 10-transformation was then applied. The log transformation attenuates the positive skew in the distributions of the MFI and chemokine concentrations and makes the normality assumption more defensible. One-way fixed-effect ANOVA models were fit to the log-transformed concentrations. Pairwise group comparisons were conducted using the method of Tukey's Honestly Significant Difference (HSD). A 0.05 level was used to determine statistically significant differences. In plots, bar values with the same letter(s) were not significantly different. ($p > 0.05$). All analyses were conducted using ATP (Version 10.0, SAS, Cary, NC).

Two assays were used to demonstrate the killing effects of 255 nm and 405 nm LED treatment on E. faecalis. The first assay assessed the killing effect of LED on a lawn of E. faecalis on TSBYE agar. 255 nm LED killed E. faecalis at 30, 60, and 90 seconds exposure, and no growth was seen in the areas of LED treatment after the treated plates were incubated overnight at 37° C. There was no killing of the untreated 0 seconds control. In contrast, 405 nm LED did not kill E. faecalis at 0, 30, 60, and 90 seconds exposure, and growth was seen in all areas of LED treatment after the plates were incubated overnight at 37° C.

To quantitate the effects of 255 nm and 405 nm LED treatment on microbial viability, E. faecalis was spotted onto 0.22 μm discs, treated, suspended in 1.0 ml TSBYE broth, plated onto TSBYE agar, and incubated overnight at 37° C. 255 nm LED treatment significantly ($p < 0.05$) reduced E. faecalis viability at 30, 60, and 90 seconds exposure. There was no significant killing by 405 nm LED treatment at 0, 30, 60, and 90 seconds exposure.

Figure 12:
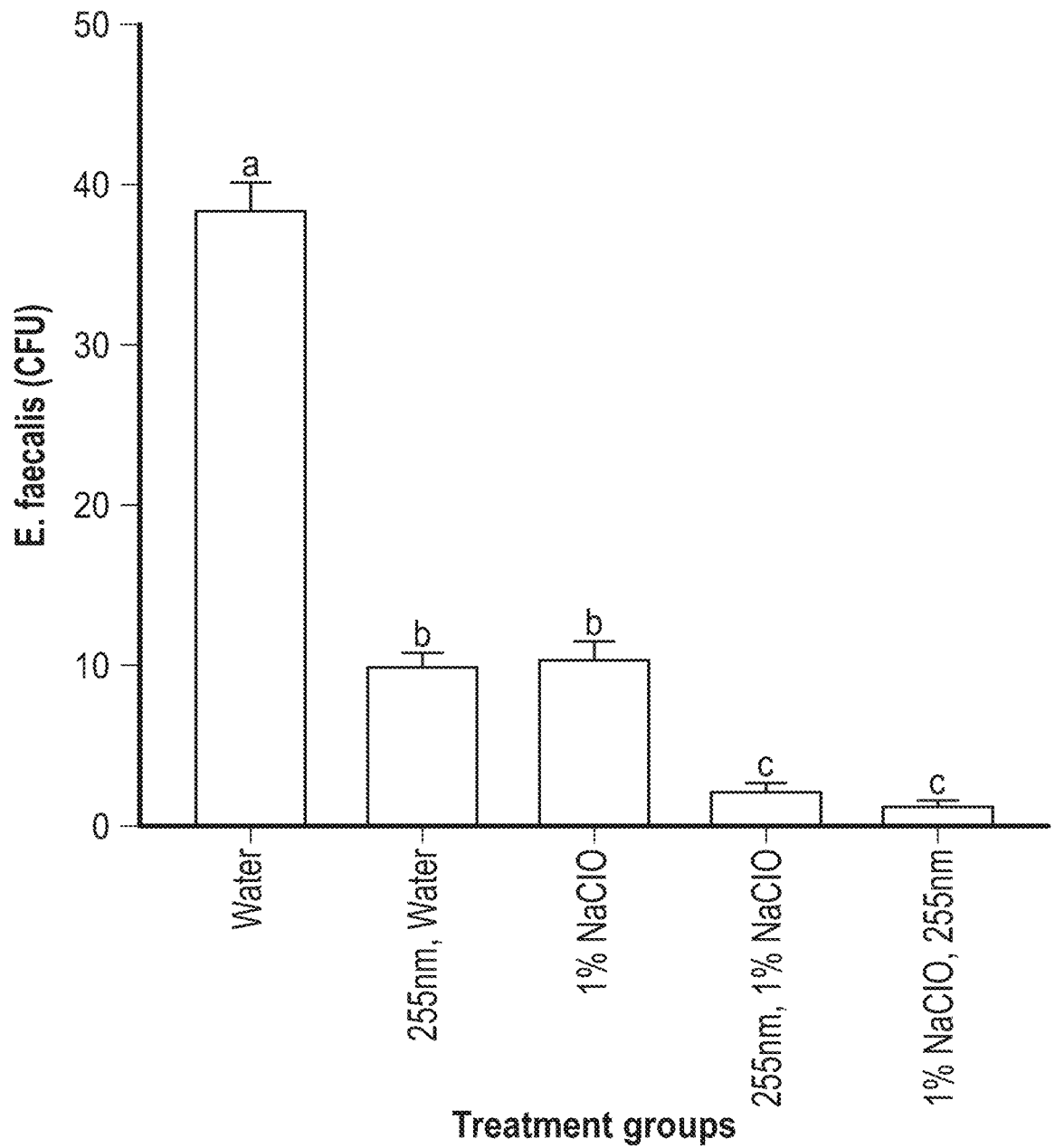
FIG. 12 illustrates, by way of example, a plot of *E. faecalis* vs treatment group.

FIG. 12 illustrates, by way of example, a plot of E. faecalis vs treatment group. E. faecalis remained viable in control treatments (38.1±1.6 SEM CFU, n=18). In comparison, E. faecalis treated with 255 nm LED had significantly less CFU (9.8±0.7 SEM CFU, n=18, $p < 0.05$) and E. faecalis treated with 1% NaClO had significantly less CFU (10.1±1.2 SEM CFU, n=18, $p < 0.05$). E. faecalis treated with 255 nm LED followed by 1% NaClO also had significantly less CFU (2.1±0.4 SEM CFU, n=18, $p < 0.05$) and E. faecalis treated with 1% NaClO followed by 255 nm LED had significantly less CFU (1.2±0.3 SEM CFU, n=18, $p < 0.05$).

FIG. 13A illustrates MFI vs time for HEPM cells after 255 nm treatment. FIG. 13B illustrates MFI vs time for fibroblasts after 255 nm treatment. FIG. 13C illustrates MFI vs time for HEPM cells after 405 nm treatment. FIG. 13D illustrates MFI vs time for fibroblasts after 405 nm treatment. To assess the effects of 255 nm and 405 nm LED treatment on cell metabolism, adhered HEPM cell and gingival fibroblast monolayers were treated with 255 nm or 405 nm LED for 0, 30, 60, and 90 seconds and cultured with tissue culture media containing resazurin. At 16 hours of incubation, there were no significant differences ($p > 0.05$) among the log 10 transformed MFI values of resorufin for either HEPM cells (FIGS. 13A, 13C) or gingival fibroblasts (FIGS. 13B, 13D) after 255 nm (FIGS. 13A, 13B) or 405 nm LED treatments (FIGS. 13C, 13D).

Figure 14D:
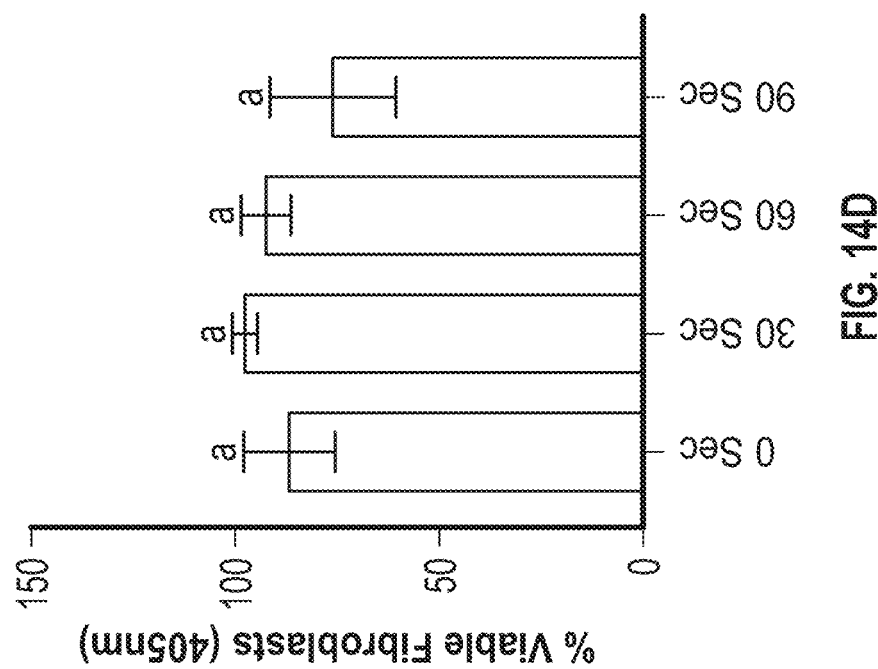
FIG. 14D illustrates % of viable fibroblasts vs time after 405 nm treatment.
Figure 14C:
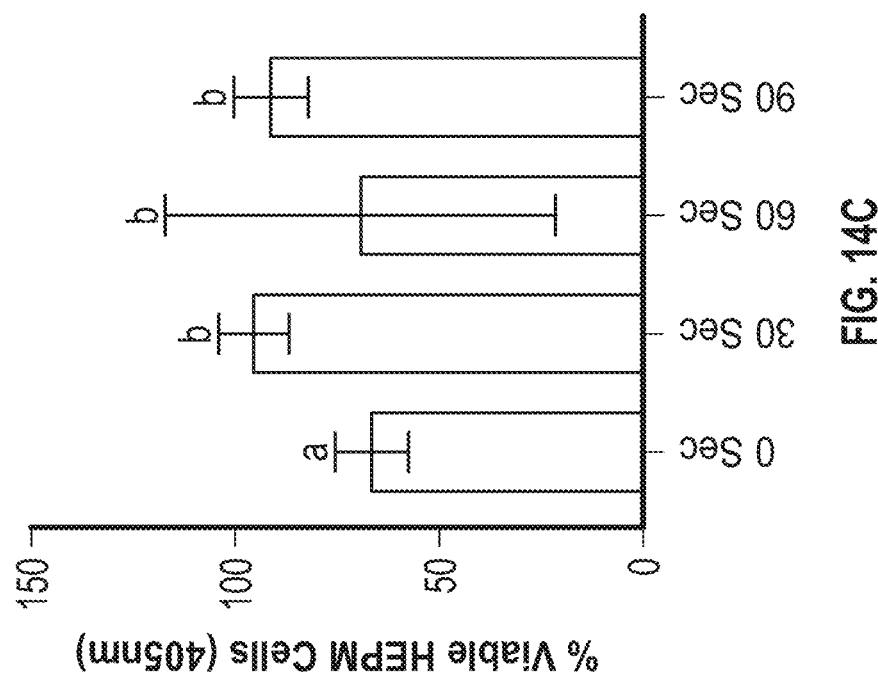
FIG. 14C illustrates % of viable HEPM cells vs time after 405 nm treatment.

FIG. 14A illustrates % of viable HEPM cells vs time after 255 nm treatment. FIG. 14B illustrates % of viable fibroblasts vs time after 255 nm treatment. FIG. 14C illustrates % of viable HEPM cells vs time after 405 nm treatment. FIG. 14D illustrates % of viable fibroblasts vs time after 405 nm treatment. To assess the effects of 255 nm and 405 nm LED treatment on HEPM cell and fibroblast viability, adhered HEPM cell and fibroblast monolayers were treated with 255 nm or 405 nm LED for 0, 30, 60, and 90 seconds and incubated with LIVE/DEAD working solution. At 45 minutes of incubation, there were no significant differences ($p > 0.05$) among the log 10 transformed MFI values of HEPM cells (FIGS. 14A, 14C) or gingival fibroblasts (FIGS. 14B, 14D) after 255 nm (FIGS. 14A, 14B) or 405 nm (FIGS. 14C, 14D) LED treatment.

Figure 15B:
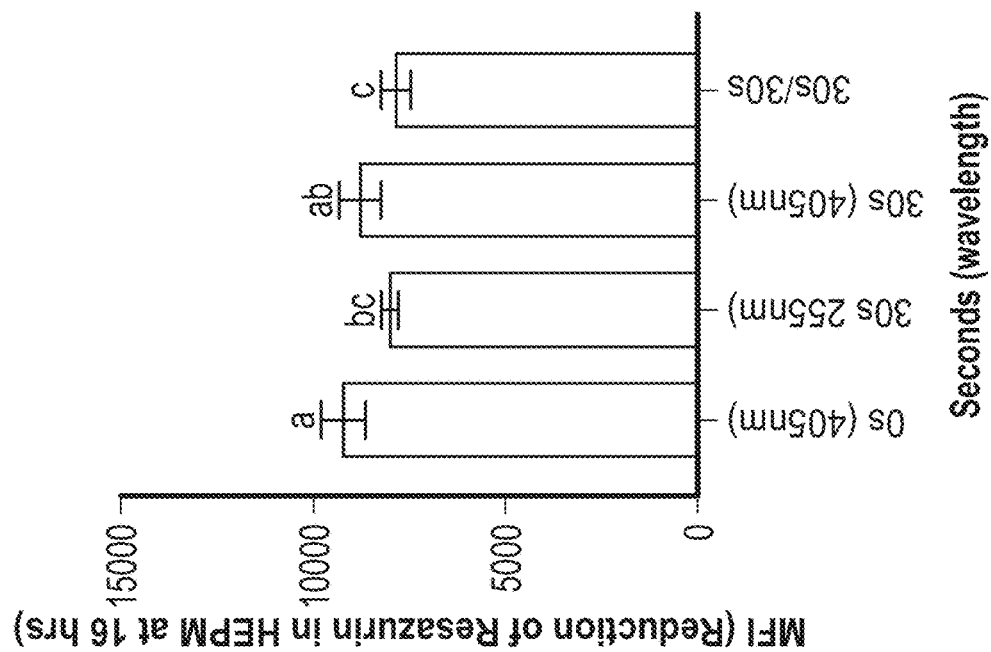
FIG. 15B illustrates MFI vs time for HEPM cells after combination treatment with 255 nm and 405 nm wavelength electromagnetic energy.
Figure 15A:
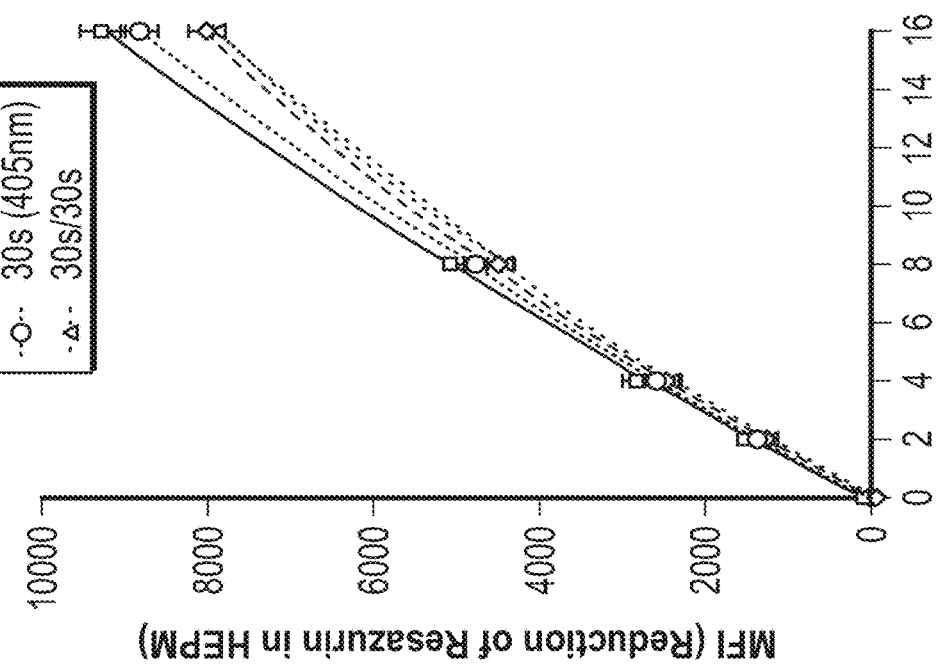
FIG. 15A illustrates MFI vs time for HEPM cells after combination treatment with 255 nm and 405 nm wavelength electromagnetic energy.
Figure 15F:
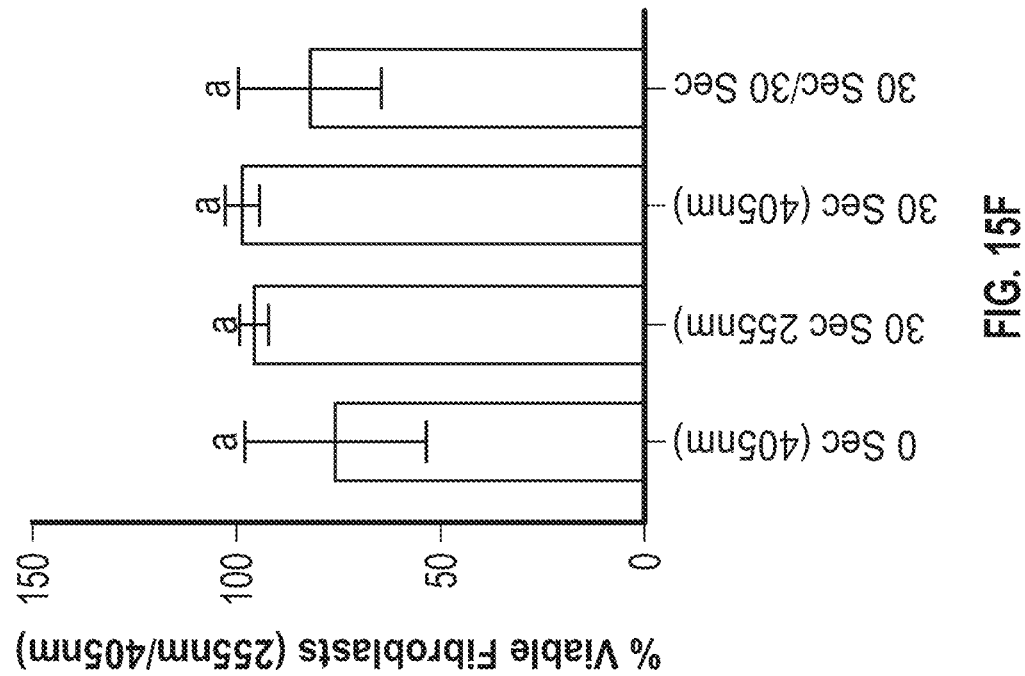
FIG. 15F illustrates % of viable fibroblast cells vs time after combination treatment with 255 nm and 405 nm wavelength electromagnetic energy.
Figure 15E:
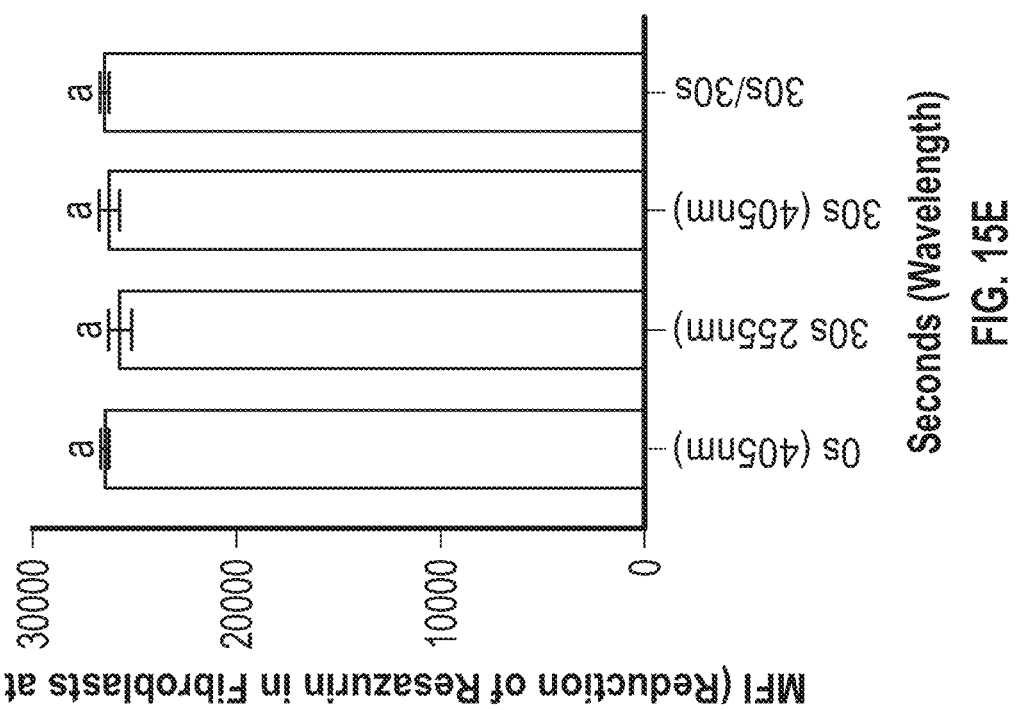
FIG. 15E illustrates MFI vs time for fibroblast cells after combination treatment with 255 nm and 405 nm wavelength electromagnetic energy.

FIG. 15A illustrates MFI vs time for HEPM cells after combination treatment with 255 nm and 405 nm wavelength electromagnetic energy. FIG. 15B illustrates MFI vs time for HEPM cells after combination treatment with 255 nm and 405 nm wavelength electromagnetic energy. FIG. 15C illustrates % of viable HEPM cells vs time after combination treatment with 255 nm and 405 nm wavelength electromagnetic energy. FIG. 15D illustrates MFI vs time for fibroblast cells after combination treatment with 255 nm and 405 nm wavelength electromagnetic energy. FIG. 15E illustrates MFI vs time for fibroblast cells after combination treatment with 255 nm and 405 nm wavelength electromagnetic energy. FIG. 15F illustrates % of viable fibroblast cells vs time after combination treatment with 255 nm and 405 nm wavelength electromagnetic energy.

To assess the effects of combination LED treatment on HEPM cell and fibroblast metabolism, adhered HEPM cell and fibroblast monolayers were treated with 255 nm LED for 30 seconds, 405 nm LED for 30 seconds, and a combination of 255 nm LED for 30 seconds followed by 405 nm LED for 30 seconds, and cultured with tissue culture media containing resazurin. At 16 hours of incubation, there were no significant differences ($p>0.05$) among the log 10 transformed MFI values of resorufin for either HEPM cells (FIGS. 15A, 15B) or fibroblasts (FIGS. 15D, 15E) after combination LED treatment.

To assess the effects of combination LED treatment on HEPM cell and fibroblast viability, adhered HEPM cell and fibroblast monolayers were treated with 255 nm LED for 30 seconds, 405 nm LED for 30 seconds, and a combination of 255 nm LED for 30 seconds followed by 405 nm LED for 30 seconds and incubated with LIVE/DEAD working solution. At 45 minutes of incubation, there were no significant differences ($p>0.05$) among the log 10 transformed MFI values of HEPM cells (FIG. 15C) or fibroblasts (FIG. 15F) after combination LED treatment.

To assess the effects of LED treatment on the production of cell biomarkers, adhered HEPM cell and gingival fibroblast monolayers were treated with 255 nm LED for 30 seconds, 405 nm LED for 30 seconds, and a combination of 255 nm LED for 30 seconds followed by 405 nm LED for 30 seconds and cell culture media was added back to each well. At 0, 24, and 48 hours post-LED treatment, media was removed and saved to assess osteoinductive, angiogenic, proliferative, and proinflammatory regenerative biomarkers. LIVE/DEAD working solution was added back to each well.

At each time point, there were no differences in the morphologies of HEPM cells or gingival fibroblasts treated with 255 nm, 405 nm, or 255 nm/405 nm LED. There was a small drop in cell viability and the LIVE/DEAD assay revealed that the cells were still 80-90% viable (data not shown).

HEPM cell and gingival fibroblasts (n 3 replications per group) produced osteoinductive, angiogenic, proliferative, and proinflammatory biomarkers 0-48 hours (Table 1). Concentrations of biomarkers produced by both cell types continued to increase over time. At 48 hours, HEPM cells and gingival fibroblasts produced low concentrations of proliferative factors (1.07-2.37 pg/ml EGF and TGFα), low concentrations of osteoinductive factors (5.97-18.67 pg/ml BMP-2, BMP-4, and BMP-9), and moderate concentrations of osteoinductive factors (184.07-227.83 pg/ml BMP-10). HEPM cells and gingival fibroblasts also produced low (1.13-1.73 pg/ml TNFα), moderate (118.90-187.73 pg/ml IL6), and high (2054.40-2382.03 pg/ml IL8) concentrations of proinflammatory factors and low (5.70-7.20 pg/ml PDGF-AB), moderate (45.03-194.80 pg/ml FGF-acidic and PIGF), and high (1744.33-3542.00 pg/ml VEGFA) concentrations of angiogenic factors.

TABLE 1

24-hour biomarker response of HEPM cells and fibroblasts to 255 nm (30 sec), 405 nm (30 sec), and 255/405 nm (30 sec each) LED exposure

| Biomarker | Hours | Cells not treated with LED | Cells treated with 255 nm LED | Cells treated with 405 nm LED | Cells treated with 255/405 nm LED |
|---|---|---|---|---|---|
| HEPM cell osteoinductive factors | | | | | |
| BMP-2 | 24 | 0.4735 | 0.5469 | 0.7816 | 0.5012 |
| | | 0.0894 | 0.0894 | 0.0894 | 0.0843 |
| | | A | A | A | A |
| BMP-4 | 24 | 1.18 | 1.074 | 1.118 | 1.165 |
| | | 0.0515 | 0.0515 | 0.0515 | 0.0486 |
| | | A | A | A | A |
| BMP-9 | 24 | 0.4203 | 0.4656 | 0.3934 | 0.4153 |
| | | 0.0222 | 0.0222 | 0.0222 | 0.0209 |
| | | A | A | A | A |
| BMP-10 | 24 | 0.8832 | 0.9178 | 0.9762 | 0.9037 |
| | | 0.1271 | 0.1271 | 0.1271 | 0.1198 |
| | | A | A | A | A |
| HEPM cell angiogenic factors | | | | | |
| VEGF | 24 | 1.946 | 2.093 | 1.923 | 2.009 |
| | | 0.0303 | 0.0303 | 0.0303 | 0.0286 |
| | | B | A | B | AB |
| PDGF-AB | 24 | 0.9889 | 0.9142 | 0.9387 | 1.036 |
| | | 0.0573 | 0.0573 | 0.0573 | 0.054 |
| | | A | A | A | A |
| FGF-acidic | 24 | 1.778 | 1.676 | 1.705 | 1.675 |
| | | 0.0242 | 0.0242 | 0.0242 | 0.0229 |
| | | A | B | AB | B |
| PIGF | 24 | 1.155 | 1.157 | 1.134 | 1.108 |
| | | 0.0169 | 0.0169 | 0.0169 | 0.0159 |
| | | A | A | A | A |
| HEPM cell proliferation factors | | | | | |
| EGF | 24 | 0.1424 | 0.1391 | 0.1253 | 0.1224 |
| | | 0.0232 | 0.0232 | 0.0231 | 0.0219 |
| | | A | A | A | A |
| TGFα | 24 | 0 | 0 | 0 | 0 |
| | | 0 | 0 | 0 | 0 |
| | | A | A | A | A |
| HEPM cell proinflammatory factors | | | | | |
| IL-6 | 24 | 1.571 | 1.64 | 1.541 | 1.688 |
| | | 0.0279 | 0.0279 | 0.0279 | 0.0263 |
| | | B | AB | B | A |
| IL-8 | 24 | 3.159 | 3.181 | 3.151 | 3.18 |
| | | 0.0413 | 0.0413 | 0.0413 | 0.0389 |
| | | A | A | A | A |
| TNFα | 24 | 0.1836 | 0.1199 | 0.0605 | 0.2089 |
| | | 0.0463 | 0.0463 | 0.0463 | 0.0436 |
| | | A | A | A | A |
| Fibroblast osteoinductive factor | | | | | |
| BMP-2 | 24 | 0.3848 | 0.4343 | 0.5208 | 0.4724 |
| | | 0.1006 | 0.0949 | 1.006 | 0.0949 |
| | | A | A | A | A |
| BMP-4 | 24 | 1.361 | 1.364 | 1.308 | 1.388 |
| | | 0.0188 | 0.0177 | 0.0188 | 0.0177 |
| | | AB | AB | B | A |
| BMP-9 | 24 | 0.2818 | 0.3432 | 0.2651 | 0.3382 |
| | | 0.0177 | 0.0167 | 0.0177 | 0.0167 |
| | | AB | A | B | A |
| BMP-10 | 24 | 0.9926 | 0.989 | 0.7171 | 1.043 |
| | | 0.1072 | 0.1011 | 0.1072 | 0.1011 |
| | | A | A | A | A |
| Fibroblast angiogenic factors | | | | | |
| VEGF | 24 | 2.917 | 2.852 | 2.91 | 2.86 |
| | | 0.0148 | 0.014 | 0.0148 | 0.014 |
| | | A | C | AB | BC |
| PDGF-AB | 24 | 1.278 | 1.224 | 1.228 | 1.238 |
| | | 0.029 | 0.0273 | 0.029 | 0.0273 |
| | | A | A | A | A |
| FGF-acidic | 24 | 1.467 | 1.38 | 1.31 | 1.381 |
| | | 0.0333 | 0.0314 | 0.0333 | 0.0314 |
| | | A' | AB | B | AB |
| PIGF | 24 | 1.517 | 1.553 | 1.532 | 1.58 |
| | | 0.0088 | 0.0083 | 0.0088 | 0.0083 |
| | | C | AB | BC | A |

TABLE 1-continued 24-hour biomarker response of HEPM cells and fibroblasts to 255 nm (30 sec), 405 nm (30 sec), and 255/405 nm (30 sec each) LED exposure

| Biomarker | Hours | Cells not treated with LED | Cells treated with 255 nm LED | Cells treated with 405 nm LED | Cells treated with 255/405 nm LED |
|---|---|---|---|---|---|
| Fibroblast proliferation factors | | | | | |
| EGF | 24 | 0.251 | 0.2153 | 0.194 | 0.2438 |
| | | 0.0221 | 0.0209 | 0.0221 | 0.0209 |
| | | A | A | A | A |
| TGFα | 24 | 0 | 0 | 0 | 0 |
| | | 0 | 0 | 0 | 0 |
| | | A | A | A | A |
| Fibroblast proinflammatory factors | | | | | |
| IL-6 | 24 | 2.783 | 3.032 | 2.788 | 3.061 |
| | | 0.0279 | 0.0263 | 2.788 | 3.061 |
| | | B | A | B | A |
| IL-8 | 24 | 3.386 | 3.408 | 3.213 | 3.362 |
| | | 0.0678 | 0.0639 | 0.0678 | 0.0639 |
| | | A | A | A | A |
| TNFα | 24 | 0.4436 | 0.4746 | 0.4411 | 0.5177 |
| | | 0.044 | 0.0415 | 0.044 | 0.0415 |
| | | A | A | A | A |

The mean and SEM of the log10 biomarker response are listed. Means not connected by the same letter are significantly different ($p < 0.05$).

In the first series of experiments (n=9 replications per group), 255 nm and 255 nm/405 nm combination LED induced production of biomarkers at 24 hours post-LED exposure (Table 1). There were significant differences ($p<0.05$) in IL6, IL8, and VEGFA in HEPM cells at 24 hours and there were significant differences ($p<0.05$) in IL6, PlGF, and BMP9 in gingival fibroblasts at 24 hours.

In the second series of experiments (n=3 replications per group), 255 nm and 255 nm/405 nm combination LED induced production of biomarkers at 0-48 hours post-LED exposure (Table 2). There were significant differences ($p<0.05$) in TNFα, IL6, VEGFA, BMP10, and PlGF at 24 hours and IL6 and BMP10 at 48 hours in HEPM cells post-LED exposure. There were significant differences ($p<0.05$) in TGFα at 24 hours and IL6 and FGF-acidic in gingival fibroblasts at 48 hours post-LED exposure.

TABLE 2

0, 24, and 48-hour biomarker response of HEPM cells and fibroblasts to 255 nm (30 sec), 405 nm (30 sec), and 255/405 nm (30 sec ea) LED exposure.

| Bio-marker | Hours | Cells not treated with LED | Cells treated with 255 nm LED | Cells treated with 405 nm LED | Cells treated with 255/405 nm LED |
|---|---|---|---|---|---|
| HEPM cell osteoinductive factors | | | | | |
| BMP-2 | 0 | | | | |
| | 24 | 1.2250 | 1.2200 | 1.2220 | 1.2460 |
| | | 0.0242 | 0.0242 | 0.0242 | 0.0242 |
| | | A | A | A | A |
| | 48 | 1.2920 | 1.3690 | 1.3050 | 1.3570 |
| | | 0.0281 | 0.0281 | 0.0281 | 0.0281 |
| | | A | A | A | A |
| BMP-4 | 0 | | | | |
| | 24 | 0.9746 | 0.9830 | 0.9533 | 1.0260 |
| | | 0.0361 | 0.0361 | 0.0361 | 0.0361 |
| | | A | A | A | A |
| | 48 | 1.0390 | 1.0900 | 1.0400 | 1.0820 |
| | | 0.0402 | 0.0402 | 0.0402 | 0.0402 |
| | | A | A | A | A |
| BMP-9 | 0 | | | | |
| | 24 | 1.3260 | 1.3090 | 1.2670 | 1.2010 |
| | | 0.0328 | 0.0328 | 0.0328 | 0.0328 |
| | | A | A | A | A |
| | 48 | 1.0370 | 0.8376 | 0.8410 | 1.0920 |
| | | 0.0861 | 0.0861 | 0.0861 | 0.0861 |
| | | A | A | A | A |
| BMP-10 | 0 | | | | |
| | 24 | 2.4210 | 2.4460 | 2.4260 | 2.3870 |
| | | 0.0100 | 0.0100 | 0.0100 | 0.0100 |
| | | AB | A | AB | B |
| | 48 | 2.3580 | 2.2450 | 2.3040 | 2.3320 |
| | | 0.0200 | 0.0200 | 0.0200 | 0.0200 |
| | | A | B | AB | AB |
| HEPM cell angiogenic factors | | | | | |
| VEGF | 0 | | | | |
| | 24 | 3.1050 | 3.1270 | 3.1020 | 2.7300 |
| | | 0.0703 | 0.0703 | 0.0703 | 0.0703 |
| | | A | A | AB | B |
| | 48 | 3.2240 | 3.0870 | 3.0720 | 3.2610 |
| | | 0.0787 | 0.0787 | 0.0787 | 0.0787 |
| | | A | A | A | A |
| PDGF-AB | 0 | | | | |
| | 24 | 0.9034 | 0.8761 | 0.8711 | 0.9301 |
| | | 0.0302 | 0.0302 | 0.0302 | 0.0302 |
| | | A | A | A | A |
| | 48 | 0.8257 | 0.8761 | 0.9113 | 0.8497 |
| | | 0.0347 | 0.0347 | 0.0347 | 0.0347 |
| | | A | A | A | A |
| FGF-acidic | 0 | | | | |
| | 24 | 1.8290 | 1.7660 | 1.7600 | 1.7840 |
| | | 0.0216 | 0.0216 | 0.0216 | 0.0216 |
| | | A | A | A | A |
| | 48 | 1.7570 | 1.7410 | 1.7260 | 1.7970 |
| | | 0.0272 | 0.0272 | 0.0272 | 0.0272 |
| | | A | A | A | A |
| PlGF | 0 | | | | |
| | 24 | 1.4360 | 1.4450 | 1.3980 | 1.1620 |
| | | 0.0521 | 0.0521 | 0.0521 | 0.0521 |
| | | A | A | A | B |
| | 48 | 1.9620 | 1.8400 | 1.8860 | 1.7950 |
| | | 0.0521 | 0.0521 | 0.0521 | 0.0521 |
| | | A | A | A | A |
| HEPM cell proliferative factors | | | | | |
| EGF | 0 | | | | |
| | 24 | 0.5328 | 0.5328 | 0.5244 | 0.5369 |
| | | 0.0047 | 0.0047 | 0.0047 | 0.0047 |
| | | A | A | A | A |
| | 48 | 0.5328 | 0.5348 | 0.5328 | 0.5348 |
| | | 0.0042 | 0.0042 | 0.0042 | 0.0042 |
| TGFα | 0 | | | | |
| | 24 | 0.3183 | 0.3380 | 0.3434 | 0.3183 |
| | | 0.0148 | 0.0148 | 0.0148 | 0.0148 |
| | | A | A | A | A |
| | 48 | 0.3164 | 0.2854 | 0.2734 | 0.3336 |
| | | 0.0171 | 0.0171 | 0.0171 | 0.0171 |
| | | A | A | A | A |
| HEPM cell proinflammatory factors | | | | | |
| IL-6 | 0 | | | | |
| | 24 | 2.1210 | 2.3220 | 2.1260 | 2.3820 |
| | | 0.0353 | 0.0353 | 0.0353 | 0.0353 |
| | | B | A | B | A |
| | 48 | 2.0770 | 2.4200 | 2.1240 | 2.2970 |
| | | 0.0649 | 0.0649 | 0.0649 | 0.0649 |
| | | B | A | B | AB |

TABLE 2-continued 0, 24, and 48-hour biomarker response of HEPM cells and fibroblasts to 255 nm (30 sec), 405 nm (30 sec), and 255/405 nm (30 sec ea) LED exposure.

| Bio-marker | Hours | Cells not treated with LED | Cells treated with 255 nm LED | Cells treated with 405 nm LED | Cells treated with 255/405 nm LED |
|---|---|---|---|---|---|
| IL-8 | 0 | | | | |
| | 24 | 3.2560 | 3.2000 | 3.2800 | 3.3720 |
| | | 0.0506 | 0.0506 | 0.0506 | 0.0506 |
| | | A | A | A | A |
| | 48 | 3.3080 | 3.3200 | 3.3210 | 3.3640 |
| | | 0.0570 | 0.0570 | 0.0570 | 0.0570 |
| | | A | A | A | A |
| TNFα | 0 | | | | |
| | 24 | 0.2732 | 0.2936 | 0.2936 | 0.3874 |
| | | 0.0194 | 0.0194 | 0.0194 | 0.0194 |
| | | B | B | B | A |
| | 48 | 0.3234 | 0.4037 | 0.3139 | 0.3446 |
| | | 0.0332 | 0.0332 | 0.0332 | 0.0322 |
| | | A | A | A | A |
| Fibroblast osteoinductive factors | | | | | |
| BMP-2 | 0 | | | | |
| | 24 | 1.0840 | 1.1200 | 1.1250 | 1.1470 |
| | | 0.0271 | 0.0271 | 0.0271 | 0.0271 |
| | | A | A | A | A |
| | 48 | 1.1240 | 1.1630 | 1.1180 | 1.1420 |
| | | 0.0287 | 0.0287 | 0.0287 | 0.0287 |
| | | A | A | A | A |
| BMP-4 | 0 | | | | |
| | 24 | 1.0420 | 1.0930 | 1.0950 | 1.1100 |
| | | 0.0215 | 0.0215 | 0.0215 | 0.0215 |
| | | A | A | A | A |
| | 48 | 1.1280 | 1.1390 | 1.1470 | 1.0900 |
| | | 0.0249 | 0.0249 | 0.0249 | 0.0249 |
| | | A | A | A | A |
| BMP-9 | 0 | | | | |
| | 24 | 1.2910 | 1.3560 | 1.2830 | 1.3400 |
| | | 0.0414 | 0.0414 | 0.0414 | 0.0414 |
| | | A | A | A | A |
| | 48 | 0.8232 | 0.8339 | 0.8735 | 0.9444 |
| | | 0.1444 | 0.1444 | 0.1444 | 0.1444 |
| | | A | A | A | A |
| BMP-10 | 0 | | | | |
| | 24 | 2.4190 | 2.4490 | 2.4140 | 2.4200 |
| | | 0.0126 | 0.0126 | 0.0126 | 0.0126 |
| | | A | A | A | A |
| | 48 | 2.2580 | 2.3000 | 2.2930 | 2.3050 |
| | | 0.0497 | 0.0497 | 0.0497 | 0.0497 |
| | | A | A | A | A |
| Fibroblast angiogenic factors | | | | | |
| VEGF | 0 | | | | |
| | 24 | 3.1210 | 3.1500 | 3.1380 | 3.0590 |
| | | 0.0513 | 0.0513 | 0.0513 | 0.0513 |
| | | A | A | A | A |
| | 48 | 3.5410 | 3.5080 | 3.6040 | 3.5000 |
| | | 0.0618 | 0.0618 | 0.0618 | 0.0618 |
| | | A | A | A | A |
| PDGF-AB | 0 | | | | |
| | 24 | 0.9595 | 1.0280 | 0.9922 | 0.9580 |
| | | 0.0519 | 0.0519 | 0.0519 | 0.0519 |
| | | A | A | A | A |
| | 48 | 0.9046 | 0.9301 | 0.9301 | 0.9209 |
| | | 0.0464 | 0.0464 | 0.0464 | 0.0464 |
| | | A | A | A | A |
| FGF-acidic | 0 | | | | |
| | 24 | 1.7740 | 1.7690 | 1.7580 | 1.7870 |
| | | 0.0298 | 0.0298 | 0.0298 | 0.0298 |
| | | A | A | A | A |
| | 48 | 1.6630 | 1.6550 | 1.6630 | 1.7330 |
| | | 0.0093 | 0.0093 | 0.0093 | 0.0093 |
| | | B | B | B | A |
| PlGF | 0 | | | | |
| | 24 | 1.7070 | 1.7190 | 1.7500 | 1.7140 |
| | | 0.0190 | 0.0190 | 0.0190 | 0.0190 |
| | | A | A | A | A |
| | 48 | 2.2920 | 2.2340 | 2.2190 | 2.0900 |
| | | 0.0518 | 0.0518 | 0.0518 | 0.0518 |
| | | A | A | A | A |
| Fibroblast proliferative factors | | | | | |
| EGF | 0 | | | | |
| | 24 | 0.5390 | 0.5390 | 0.5390 | 0.5564 |
| | | 0.0054 | 0.0054 | 0.0054 | 0.0054 |
| | | A | A | A | A |
| | 48 | 0.5327 | 0.5473 | 0.5431 | 0.5431 |
| | | 0.0058 | 0.0058 | 0.0058 | 0.0058 |
| | | A | A | A | A |
| TGFα | 0 | | | | |
| | 24 | 0.3281 | 0.3945 | 0.3585 | 0.4031 |
| | | 0.0107 | 0.0107 | 0.0107 | 0.0107 |
| | | B | A | AB | A |
| | 48 | 0.3768 | 0.3677 | 0.3670 | 0.3380 |
| | | 0.0154 | 0.0154 | 0.0154 | 0.0154 |
| | | A | A | A | A |
| Fibroblast proinflammatory factors | | | | | |
| IL-6 | 0 | | | | |
| | 24 | 2.2600 | 2.4980 | 2.2300 | 2.6180 |
| | | 0.1286 | 0.1286 | 0.1286 | 0.1286 |
| | | A | A | A | A |
| | 48 | 2.2730 | 2.6490 | 2.3110 | 2.6960 |
| | | 0.0616 | 0.0616 | 0.0616 | 0.0616 |
| | | B | A | B | A |
| IL-8 | 0 | | | | |
| | 24 | 3.3060 | 3.3750 | 3.4070 | 3.3770 |
| | | 0.0687 | 0.0687 | 0.0687 | 0.0687 |
| | | A | A | A | A |
| | 48 | 3.3510 | 3.4620 | 3.4790 | 3.4090 |
| | | 0.0680 | 0.0680 | 0.0680 | 0.0680 |
| | | A | A | A | A |
| TNFα | 0 | | | | |
| | 24 | 0.3604 | 0.4193 | 0.3683 | 0.3446 |
| | | 0.0398 | 0.0398 | 0.0398 | 0.0398 |
| | | A | A | A | A |
| | 48 | 0.4330 | 0.4649 | 0.4486 | 0.4264 |
| | | 0.0457 | 0.0457 | 0.0457 | 0.0457 |
| | | A | A | A | A |

The mean and SEM of the log10 biomarker response are listed. Means not connected by the same letter are significantly different ($p < 0.05$).

Methods to assist in the resolution of endodontic tissue infection and inflammation after chemo-mechanical debridement of canal spaces reduce infections, regenerate tissues, lessen pain, and improve overall patient recovery. These methods include the use of LED treatment to assist in the sterilization of canal spaces and induce the production of biomarkers to initiate endodontic tissue regeneration. In this study, it was shown that 255 nm and 405 nm LED light could facilitate these processes. It was demonstrated that 1) at least 255 nm LED treatment killed E. faecalis, 2) 255 nm LED and NaClO efficiently killed E. faecalis, 3) neither 255 nm nor 405 nm LED treatment affected the viability of HEPM cells and gingival fibroblasts, and 4) at least 255 nm LED treatment or 255 nm/405 nm combination LED treatment of HEPM cells and gingival fibroblasts induced the production of biomarkers related to endodontic tissue regeneration.

Evidence suggests that UVC (255 nm) and blue (400-450 nm) wavelengths of light kill many microbial species and viruses. When used at higher energy doses or for prolonged time periods, these wavelengths are also be cytotoxic to eukaryotic cells. However, at lower energy levels for shorter time periods like those used in this study, these wavelengths induce cells to release biomarkers related to tissue recovery and regeneration.

255 nm light has antimicrobial activity and is used in a variety of applications related to treating localized tissue infections. 405 nm light has time-dependent and energy dose-dependent effects on prokaryotic and eukaryotic cells. 36 J/cm² is antimicrobial to prokaryotic microorganisms but not cytotoxic to eukaryotic cells. 54 J/cm² is cytotoxic to eukaryotic cells. The antimicrobial and cytotoxic mechanisms involve reactive oxygen species related to oxidative stress, $H_2O_2$ generation, and other ROS, all contributing to cellular damage. Together, this information suggests that there is increased susceptibility of prokaryotic microorganisms compared to eukaryotic cells that could lead to a treatment modality to preferentially inactivate microorganisms in infected tissues.

The potential for LED to induce the production of biomarkers related to tissue recovery and regeneration is equally novel and important. Work with low level laser irradiation has been shown to promote proliferation of mesenchymal cells, cardiac stem cells, bone marrow stem cells, and dental pulp stem cells. Low level laser irradiation also promotes bone marrow stem cell growth factor secretion, myogenic differentiation, accelerates pulp healing, and bone sialoprotein expression. Lasers also activate TGF-β1 in dental pulp stem cells.

The production of osteoinductive, angiogenic, proliferative, and proinflammatory biomarkers are important to tissue recovery and regeneration. 13 biomarkers in various categories were studied. Osteoinductive factors included the bone morphogenic proteins (BMPs) belonging to the TGF-β superfamily of structurally related signaling proteins. There are 15 molecules (BMP-2 to BMP-14) and 4 of these proteins were selected. BMP-2 is capable of inducing bone and cartilage formation. BMP-4 is involved in the development and maintenance of bone and cartilage. BMP-9 (aka Growth/Differentiation Factor-2) is involved in the remodeling and maintenance of tissues and it inhibits endothelial cell proliferation and migration. BMP-10 is structurally related to BMP-9, and both inhibit endothelial cell proliferation and migration. For both HEPM cells and gingival fibroblasts, osteoinductive responses were minimal for BMP-2, BMP-4, and BMP-9 (5.97-18.67 pg/ml) and moderate for BMP-10 (184.07-227.83 pg/ml). Exposure of HEPM cells to 255 nm LED alone or 255 nm/405 LED produced variations in concentrations of BMP10 at 24- and 48-hours post-LED exposure (Table 1, and Table 2).

Angiogenesis is important to the regeneration of injured or infected dental tissue, and angiogenic and other growth factors are important to the reformation and survival of regenerated pulp. 5 angiogenic factors were selected. VEGFA is a potent growth and angiogenic cytokine. It stimulates proliferation and survival of endothelial cells and promotes angiogenesis and vascular permeability. PDGF-A is a potent mitogen for connective tissue cells, bone, and cartilage cells. FGF-acidic is a member of the Fibroblast Growth Factor superfamily. FGF-acidic regulates the development, restoration, and redistribution of tissue and serves as to facilitate angiogenesis, wound healing, and chronic inflammation. PlGF is an angiogenic factor that stimulates and endothelial cell proliferation and migration. HEPM cells and gingival fibroblasts produced low concentrations of PDGF-AB (5.70-7.20 pg/ml), moderate concentrations of FGF-acidic and PlGF (45.03-194.80 pg/ml), and high concentrations of VEGFA (1744.33-3542.00 pg/ml) (Table 1). Exposure of cells to 255 nm LED or 255 nm/405 combination LED produced variations in concentrations of VEGFA, PlGF, and FGF-acidic (Table 1 and Table 2). There were no significant increases in PDGF-AB, FGF-acidic, and PlGF responses for HEPM cells and VEGF, PDGF-AB, and FGF-acidic responses for fibroblasts.

Proliferation of cells is an important step to the regeneration of injured or infected dental tissues. 2 cell proliferation related factors were selected. EGF is a potent growth factor that stimulates the proliferation of various epidermal and epithelial cells and is involved in wound healing. TGFα is an EGF-related growth factor that stimulates the proliferation of a wide range of epidermal and epithelial cells. HEPM cells and fibroblasts produced low concentrations of EGF and TGFα (1.07-2.37 pg/ml). Exposure of fibroblasts to 255 nm or 255 nm/405 nm combination LED produced higher concentrations of TGFα at 24 hours post-LED exposure (Table 1 and Table 2).

Proinflammatory chemokines that chemoattracts and activates neutrophils will likely be produced and three proinflammatory factors were selected. IL6 regulates inflammatory responses and regulates bone metabolism. IL8 is a proinflammatory chemokine that chemoattracts and activates neutrophils. TNFα is a proinflammatory cytokine that plays a role in the induction of inflammation. HEPM cells and gingival fibroblasts produced low concentration of TNFα (1.13-1.73 pg/ml), moderate concentrations of IL6 (118.90-187.73 pg/ml), and high concentrations of IL8 (2054.40-2382.03 pg/ml). There were LED-induced angiogenic responses in IL6 for HEPM cells and in fibroblasts, but there were no differences in IL8 and TNFα for HEPM cells and for gingival fibroblasts (Table 1 and Table 2). Exposure of HEPM cells to 255 nm LED or 255 nm/405 LED produced variations in concentrations of TNFα, IL6, at 24 hours and IL6 at 48 hours post-LED exposure. Exposure of fibroblasts to 255 nm or 255 nm/405 nm produced higher concentrations of IL6 at 48 hours post-LED exposure.

Advances in LED technology allow concepts and methodologies to be applied in the form of a small hand-held device. This device is self-contained and consists of a hand piece with a small flexible probe to deliver 255 nm LED deep into canal depths and spaces. Short 30 second treatments of low energy doses are antimicrobial yet, minimally harmful to endodontic tissues and cells. In summary, the results in this study suggest a new treatment modality using 255 nm LED for the sterilization and regeneration of infected and inflamed endodontic tissues.

FIG. 16 shows one example of a tooth 1600 after mechanical removal of material (e.g., enamel, dentin, pulp or the like) to form one or more passages or cavities (treatment locations) within the tooth 1600. For instance, in the example shown in FIG. 16, the tooth 1600 includes a root canal 1604 bored out along each of the roots 1602 and through the upper tooth structure. As further shown in FIG. 16, the light-based dental system 100 is shown in an operative configuration, for instance, with the delivery shaft assembly 104 extending into the tooth 1600 and along one of the roots 1602. One or more distal light ports 116 (in this example a plurality) corresponding to the distal light port are provided at a variety of locations along the delivery shaft assembly 104 proximate the distal shaft profile. The delivery ports 116 facilitate the broadcast of light at one or more wavelengths from the delivery shaft assembly 104 and into the tooth 1600 or other treatment location to provide one or more therapeutic effects to features 1606 within the roots 1602 as well as the remainder of the tooth 1600.

In one example, the delivery shaft assembly 104 is manipulated by translation, rotation or the like to accordingly bathe a portion (including the entirety) of the root canal 1604 with therapeutic light delivered from the delivery ports 116. As shown in the example in FIG. 16, the delivery ports 116 are at various locations along the delivery shaft assembly 104 to facilitate the broadcast of light from the instrument shaft assembly 104 in one or more directions and one or more patterns (e.g., light profiles or patterns, broadcast profiles or patterns, or the like). In other examples, the delivery ports 116 include a single or multiple light delivery ports, for instance at a distal tip.

As also shown in FIG. 16, in one example, the tooth 1600 includes one or more features 1606. The features 1606 include, but are not limited to, one or more lateral canals, passages (for instance, extending from a main root canal 1604), crevices, fins, biofilms, collections of proteins, carbohydrates or the like. As previously described herein, biofilms, proteins, carbohydrates and the like may hide, conceal or protect one or more microorganisms therein. These features 1606 frustrate the removal or killing of microorganisms with one or more or chemical irrigants, mechanical debridement or the like. Light in one or more wavelengths, including wavelengths of 200 to 405 nanometers, 255 to 280 nanometers or the like, delivered into these features 1606 including canals, passages, crevices, fins, biofilms, proteins, carbohydrates or the like reaches difficult to access microorganisms and kills them. Optionally, light delivered from the system 100 cooperates with chemical irrigants to enhance the effectiveness of the irrigants, for instance within the features 1606.

In the configuration shown in FIG. 2, for instance, with the tooth 1600 bored out and in the process of disinfection with the light-based dental system 100, a root canal 1604 (one example of a cavity, passage, treatment location or the like) is formed, in one example, with a dental drill and one or more tools including dental files. The root canal 1604 is thereafter mechanically cleaned, for instance, by mechanical debridement with a dental file to remove dental pulp including the nerve, blood vessels or other soft tissue provided within the tooth 1600. As further shown, the tooth 1600 is optionally irrigated, for instance, with one or more bactericidal irrigants including, but not limited to, one or more of sodium hypochlorite, EDTA, chlorhexidine (CHX) or the like. These irrigants are, in some examples, found to kill microorganisms. In the example shown in FIG. 2, a surface of the irrigant 1608 is shown in the tooth 1600 with a broken line and is pooled therebelow. In other examples, the irrigant 1608 is flushed into the tooth 1600 and aspirated out.

At least a portion of the irrigant 1608 remains within the tooth 1600, for instance, along one or more of the features 1606 provided within the root canal 1604, within the main portion of the tooth 1600 or the like. In one example, the light-based dental system 100 is used in combination with the irrigant 1608. The provision of light having one or more wavelengths to the irrigant 1608, for instance, adjacent to the features 1606 generates one or more free radicals including chloride ions or the like configured to readily engage with and break down the one or more features 1606 within the tooth 1600. Because the irrigant is already present the generation of free radicals with the application of light from the light-based dental system 100 immediately applies the resulting free radicals to the features 1606 and readily breaks down one or more biofilms, proteins, carbohydrates or the like and kills microorganisms otherwise concealed within biofilms, carbohydrates, proteins or the like.

In still other examples, after mechanical debridement (removal of one or more features of the tooth 1600 including nerves, blood vessels, tissue or the like) the light-based dental system 100 is used by itself, for instance, in a configuration shown as in FIG. 16 to broadcast therapeutic light (without an irrigant) into the root canals 1604. The disbursed therapeutic broadcasting of light, for instance, from the one or more delivery ports 116 (optionally with one or more of rotational or translational manipulation) distributes one or more wavelengths of light into the root canal 1604 and the remainder of the tooth 1600 to accordingly interact with one or more of the features 1606 (e.g., side canals, irregular features such as fins, biofilms, proteins, carbohydrates or the like). The light by itself interacts with the microorganisms in the passage or cavity (and optionally within features 1606) to accomplish one or more of killing microorganisms, initiating tissue regeneration or providing a cleaned tooth 1600 ready for one or more dental procedures including filling, crowns or the like.

VARIOUS NOTES & EXAMPLES

Example 1 can include subject matter such as a light based dental treatment system comprising: a handle generator configured to generate therapeutic light, the handle generator includes: a generator housing; and at least one light element configured to generate the therapeutic light; at least one delivery shaft assembly selectively coupled with the handle generator, the at least one delivery shaft assembly includes: a delivery shaft having a proximal shaft profile and a distal shaft profile; a proximal light port; and a distal light port configured to deliver light from the delivery shaft to a treatment location Example 2 can include, or can optionally be combined with the subject matter of Example 1, to optionally include wherein the handle generator includes an alignment collet having a light passage extending along a movable interior collet profile.

Example 3 can include, or can optionally be combined with the subject matter of one or any combination of Examples 1 or 2 to optionally include wherein the interior collet profile of the alignment collet is configured to grasp the delivery shaft and align the proximal light port with at least one light element.

Example 4 can include, or can optionally be combined with the subject matter of one or any combination of Examples 1-3 to optionally include wherein the at least one light element includes one or more of an LED, laser diode, laser or quantum cascade laser.

Example 5 can include, or can optionally be combined with the subject matter of one or any combination of Examples 1-4 to optionally include wherein the light element is configured to generate therapeutic light having a wavelength between 200 to 405 nanometers.

Example 6 can include, or can optionally be combined with the subject matter of Examples 1-5 to optionally include wherein the light element is configured to generate therapeutic light having a wavelength between 255 and 280 nanometers.

Example 7 can include, or can optionally be combined with the subject matter of Examples 1-6 to optionally include wherein a conductive heat sink is coupled between the at least one light element and a generator housing of the handle generator.

Example 8 can include, or can optionally be combined with the subject matter of Examples 1-7 to optionally include wherein the generator housing includes a lens assembly interposed between the light element and the interior collet profile.

Example 9 can include, or can optionally be combined with the subject matter of Examples 1-8 to optionally include wherein the proximal shaft profile is complementary to the interior collet profile.

Example 10 can include, or can optionally be combined with the subject matter of Examples 1-9 to optionally include wherein the interior collet profile includes one or more movable shoes, feet, rings, or jaws.

Example 11 can include, or can optionally be combined with the subject matter of Examples 1-10 to optionally include wherein the at least one delivery shaft includes a shaft fitting having a fitting profile coupled with the delivery shaft, and the fitting profile is complementary to the interior collet profile of the alignment collet.

Example 12 can include, or can optionally be combined with the subject matter of Examples 1-11 to optionally include a light delivery shaft assembly comprising: a delivery shaft extending between a proximal tip and a distal tip, the delivery shaft includes: a proximal shaft profile having a proximal light port configured for reception of therapeutic light from a light element; and a distal shaft profile different than the proximal shaft profile, the distal shaft profile having a distal light port configured to deliver therapeutic light received from the proximal light port; and a shaft fitting coupled with the proximal shaft profile, the shaft fitting includes a fitting profile complementary to an interior collet profile of a handle generator, the fitting profile configured to align the proximal light port with at least one light element of the handle generator.

Example 13 can include, or can optionally be combined with the subject matter of Examples 1-12 to optionally include wherein the distal shaft profile is smaller than the proximal shaft profile.

Example 14 can include, or can optionally be combined with the subject matter of Examples 1-13 to optionally include wherein the distal shaft profile tapers from the proximal shaft profile toward the distal tip.

Example 15 can include, or can optionally be combined with the subject matter of Examples 1-14 to optionally include wherein the distal shaft profile is at a different angle relative to the proximal shaft profile.

Example 16 can include, or can optionally be combined with the subject matter of Examples 1-15 to optionally include wherein the distal shaft profile varies in one or more of size, shape or angle relative to the proximal shaft profile.

Example 17 can include, or can optionally be combined with the subject matter of Examples 1-16 to optionally include wherein the shaft fitting is pliable relative to at least the proximal shaft profile.

Example 18 can include, or can optionally be combined with the subject matter of Examples 1-17 to optionally include wherein the delivery shaft includes at least one of a fiberoptic element or hollow member having a reflective interior.

Example 19 can include, or can optionally be combined with the subject matter of Examples 1-18 to optionally include a plurality of light delivery shaft assemblies including at least first and second light delivery shaft assemblies: the first light delivery shaft assembly includes a first distal shaft profile; and the second light delivery shaft assembly includes a second distal shaft profile different from the first distal shaft profile.

Example 20 can include, or can optionally be combined with the subject matter of Examples 1-19 to optionally include wherein the shaft fitting is integral to the proximal shaft profile of the delivery shaft.

Example 21 can include, or can optionally be combined with the subject matter of Examples 1-20 to optionally include wherein the fitting profile of the shaft fitting includes a complementary shape to a shape of the interior collet profile.

Example 22 can include, or can optionally be combined with the subject matter of Examples 1-21 to optionally include a method for treating a tooth comprising: selecting a light delivery shaft assembly having a distal shaft profile corresponding to a cavity profile of the tooth; coupling the selected light delivery shaft assembly with a handle generator, coupling includes: positioning a shaft fitting of the selected light delivery shaft assembly within an alignment collet; operating the alignment collet to align a proximal light port of the delivery shaft assembly with at least one light element of the handle generator; and fixing light delivery shaft assembly to the handle generator with operation of the alignment collet.

Example 23 can include, or can optionally be combined with the subject matter of Examples 1-22 to optionally include wherein fixing the light delivery shaft assembly includes clamping an interior collet profile around a fitting profile of the shaft fitting, the fitting profile complementary to the interior collect profile.

Example 24 can include, or can optionally be combined with the subject matter of Examples 1-23 to optionally include wherein operating the alignment collet to align the proximal light port with at least one light element includes applying a plurality of opposing biases to the shaft fitting toward a light element axis of the at least one light element.

Example 25 can include, or can optionally be combined with the subject matter of Examples 1-24 to optionally include selecting a second light delivery shaft having a second distal shaft profile corresponding to another feature of the cavity profile of the tooth.

Example 26 can include, or can optionally be combined with the subject matter of Examples 1-25 to optionally include delivering therapeutic light to a treatment location of the cavity profile proximate to a distal tip of the delivery shaft to trigger microbial cell death.

Example 27 can include, or can optionally be combined with the subject matter of Examples 1-26 to optionally include delivering therapeutic light to a treatment location of the cavity profile proximate to a distal tip of the delivery shaft to trigger tissue regeneration.

Example 28 can include, or can optionally be combined with the subject matter of Examples 1-27 to optionally include delivering therapeutic light to a treatment location of the cavity profile proximate to a distal tip of the delivery shaft having one or more wavelengths between 200 and 405 nanometers.

Each of these non-limiting examples can stand on its own, or can be combined in various permutations or combinations with one or more of the other examples.

The above detailed description includes references to drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A light-based dental treatment system comprising:
a handle generator configured to generate therapeutic light, the handle generator includes:
 a handle generator housing;
 an alignment collet having a light passage extending along a movable interior collet profile; and
 at least one light element configured to generate the therapeutic light;
at least one delivery shaft assembly selectively coupled with the handle generator, the at least one delivery shaft assembly includes:
 a delivery shaft having a shaft profile with a first outer diameter;
 a shaft fitting of a pliable material combined with the delivery shaft and configured to be grasped by the alignment collet, the shaft fitting having a fitting profile with a second outer diameter than is larger than the first outer diameter;
 a proximal light port aligned with the at least one light element; and
 a distal light port configured to deliver light from the delivery shaft to a treatment location.

2. The light-based dental treatment system of claim 1, wherein the interior collet profile of the alignment collet is configured to grasp the shaft fitting and align the proximal light port with at least one light element.

3. The light-based dental treatment system of claim 1, wherein the at least one light element includes one or more of a light emitting diode (LED), laser diode, laser or quantum cascade laser.

4. The light-based dental treatment system of claim 1, wherein the light element is configured to generate therapeutic light having a wavelength between 200 to 405 nanometers.

5. The light-based dental treatment device of claim 1, wherein the light element is configured to generate therapeutic light having a wavelength between 255 and 280 nanometers.

6. The light-based dental treatment device of claim 1, wherein a conductive heat sink is coupled between the at least one light element and a generator housing of the handle generator.

7. The light-based dental treatment device of claim 1, wherein the generator housing includes a lens assembly interposed between the light element and the delivery shaft.

8. The light-based dental treatment device of claim 1, wherein the proximal shaft profile is complementary to an interior collet profile.

9. The light-based dental treatment device of claim 1, wherein an interior collet profile includes one or more movable shoes, feet, rings, or jaws configured to grasp the shaft fitting.

10. The light-based dental treatment system of claim 1 further comprising a frequency control configured to:
deliver therapeutic light through the delivery shaft to the treatment location at a first wavelength to trigger microbial cell death; and
deliver therapeutic light through the delivery shaft to the treatment location at a second wavelength to trigger tissue regeneration.

11. The light-based dental treatment system of claim 10 wherein the therapeutic light triggers microbial cell death without heat.

12. A light delivery shaft assembly comprising:
a delivery shaft extending between a proximal tip and a distal tip, the delivery shaft includes:
 a proximal shaft profile having a proximal light port configured for reception of therapeutic light from a light element; and
 a distal shaft having a first diameter and a profile different than the proximal shaft profile, the distal shaft profile having a distal light port configured to deliver therapeutic light received from the proximal light port; and
a shaft fitting combined with a portion of the proximal shaft profile, the shaft fitting includes a fitting profile having a second diameter larger than the first diameter, and complementary to and configured to be grasped by an interior collet profile of a handle generator, the fitting profile configured to align the proximal light port with at least one light element of the handle generator;
wherein the shaft fitting is pliable relative to at least the proximal shaft profile.

13. The light delivery shaft assembly of claim 12, wherein the distal shaft profile is smaller than the proximal shaft profile.

14. The light delivery shaft assembly of claim 12, wherein the distal shaft profile tapers from the proximal shaft profile toward the distal tip.

15. The light delivery shaft assembly of claim 12, wherein the distal shaft profile is at a different angle relative to the proximal shaft profile.

16. The light delivery shaft assembly of claim 12, wherein the distal shaft profile varies in one or more of size, shape or angle relative to the proximal shaft profile.

17. The light delivery shaft assembly of claim 12, wherein the delivery shaft includes at least one of a fiberoptic element or hollow member having a reflective interior.

18. The light delivery shaft assembly of claim 12 comprising a plurality of light delivery shaft assemblies including at least first and second light delivery shaft assemblies:
the first light delivery shaft assembly includes a first distal shaft profile; and
the second light delivery shaft assembly includes a second distal shaft profile different from the first distal shaft profile.

19. The light delivery shaft assembly of claim 12, wherein the shaft fitting is integral to the proximal shaft profile of the delivery shaft.

20. The light delivery shaft assembly of claim 12, wherein the fitting profile of the shaft fitting includes a complementary shape to a shape of the interior collet profile.

21. A method for treating a tooth comprising:
selecting a light delivery shaft assembly having a distal shaft profile corresponding to a cavity profile of the tooth;
coupling the selected light delivery shaft assembly with a handle generator, coupling includes:
positioning a shaft fitting of the selected light delivery shaft assembly within an alignment collet;
operating the alignment collet to align a proximal light port of the delivery shaft assembly with at least one light element of the handle generator; and
fixing light delivery shaft assembly to the handle generator with operation of the alignment collet;
delivering therapeutic light through the light delivery shaft assembly to a treatment location of the cavity profile inside a patient's mouth proximate to a distal tip of the delivery shaft at a first wavelength to trigger microbial cell death;
delivering therapeutic light through the light delivery shaft assembly to a treatment location of the cavity profile inside a patient's mouth proximate to a distal tip of the delivery shaft at a second wavelength to trigger tissue regeneration.

22. The method of claim 21, wherein fixing the light delivery shaft assembly includes clamping an interior collet profile around a fitting profile of the shaft fitting, the fitting profile complementary to the interior collect profile.

23. The method of claim 21, wherein operating the alignment collet to align the proximal light port with at least one light element includes applying a plurality of opposing biases to the shaft fitting toward a light element axis of the at least one light element.

24. The method of claim 21 comprising selecting a second light delivery shaft having a second distal shaft profile corresponding to another feature of the cavity profile of the tooth.

25. The method of claim 21 comprising delivering therapeutic light to a treatment location of the cavity profile proximate to a distal tip of the delivery shaft having one or more wavelengths between 200 and 405 nanometers.

26. The method of claim 21 comprising delivering therapeutic light to a treatment location of the cavity profile to trigger microbial cell death without heat.

* * * * *